(12) United States Patent
Wong et al.

(10) Patent No.: US 10,908,153 B2
(45) Date of Patent: Feb. 2, 2021

(54) PSEUDOMONAS AERUGINOSA INHIBITOR COMPOUNDS

(71) Applicants: Centre National de la Recherche Scientifique (CNRS), Paris (FR); Commissariat A L'Energie Atomique et Aux Energies Alternatives, Paris (FR)

(72) Inventors: Yung-Sing Wong, Saint Martin d'Hères (FR); Sophie Ple, Saint Martin d'Hères (FR); Ina Attree, Saint Martin d'Hères (FR); Caroline Barette, Sassenage (FR)

(73) Assignees: CENTRE NATIONAL DE LA RECHERCHE SCIENTIFIQUE (CNRS), Paris (FR); COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 256 days.

(21) Appl. No.: 15/744,190

(22) PCT Filed: Jul. 12, 2016

(86) PCT No.: PCT/EP2016/066550
§ 371 (c)(1),
(2) Date: Jan. 12, 2018

(87) PCT Pub. No.: WO2017/009344
PCT Pub. Date: Jan. 19, 2017

(65) Prior Publication Data
US 2018/0209969 A1     Jul. 26, 2018

(30) Foreign Application Priority Data

Jul. 13, 2015  (FR) ..................................... 15 56639

(51) Int. Cl.
| | | |
|---|---|---|
| *G01N 33/543* | (2006.01) | |
| *C07D 401/14* | (2006.01) | |
| *C07D 213/30* | (2006.01) | |
| *A61K 31/4709* | (2006.01) | |
| *A61P 31/04* | (2006.01) | |
| *A61K 31/165* | (2006.01) | |
| *A61K 31/191* | (2006.01) | |
| *A61K 31/197* | (2006.01) | |
| *A61K 31/352* | (2006.01) | |
| *A61K 31/444* | (2006.01) | |
| *A61K 31/47* | (2006.01) | |
| *A61K 31/11* | (2006.01) | |

(52) U.S. Cl.
CPC ............ *G01N 33/543* (2013.01); *A61K 31/11* (2013.01); *A61K 31/165* (2013.01); *A61K 31/191* (2013.01); *A61K 31/197* (2013.01); *A61K 31/352* (2013.01); *A61K 31/444* (2013.01); *A61K 31/47* (2013.01); *A61K 31/4709* (2013.01); *A61P 31/04* (2018.01); *C07D 213/30* (2013.01); *C07D 401/14* (2013.01)

(58) Field of Classification Search
CPC .... A61K 31/11; A61K 31/165; A61K 31/191; A61K 31/197; A61K 31/352; A61K 31/444; A61K 31/47; A61K 31/4709; A61P 31/04; C07D 213/30; C07D 401/14; G01N 33/543
See application file for complete search history.

(56) References Cited

U.S. PATENT DOCUMENTS

2012/0114633 A1* 5/2012 Moir ...................... A61K 31/16
424/130.1

FOREIGN PATENT DOCUMENTS

| WO | 2006/132583 A1 | 12/2006 |
|---|---|---|
| WO | 2008/115118 A1 | 9/2008 |
| WO | 2009/137133 A2 | 11/2009 |
| WO | 2009/140215 A2 | 11/2009 |
| WO | 2010/118046 A2 | 10/2010 |

OTHER PUBLICATIONS

Agnew et al., "Iterative In Situ Click Chemistry Creates Antibody-like Protein Capture Agents", Angewandte Chemie International Edition in English, 2009, vol. 48, No. 27, pp. 4944-4948.

Alnour et al., "Multidrug Resistant Pseudomonas (P) aeruginosa: Medical Impact, Pathogenicity, Resistance Mechanisms and Epidemiology," JSM Microbiology, 2017, vol. 5, No. 3. (8 pages).

Barbier et al., "Multirésistance chez Pseudomonas aeruginosa. Vers l'impasse thérapeutique?" Medecine/Sciences, 2010, Bol. 26, pp. 960-968. (with English Abstract).

Clunes et al., "Cystic fibrosis: the mechanisms of pathogenesis of an inherited lung disorder", Drug Discovery Today: Disease Mechanisms, 2007, vol. 4, No. 2, pp. 63-72.

Cornelis, Guy R., "The type III injectisome", Nature Reviews Microbiology, Dec. 2006, vol. 4, No. 11, pp. 811-825.

Coutrot et al., "Controlling the Chair Conformation of a Mannopyranose in a Large-Amplitude [2]Rotaxane Molecular Machine", Chemistry: A European Journal, 2009, vol. 15, pp. 5186-5190.

(Continued)

*Primary Examiner* — Galina M. Yakovleva
(74) *Attorney, Agent, or Firm* — Buchanan Ingersoll & Rooney PC

(57) ABSTRACT

The invention relates to a method of identifying molecules which inhibit the virulence machinery of *Pseudomonas aeruginosa*, to a device for identifying a molecule which inhibits the virulence machinery of *Pseudomonas aeruginosa*, to novel compounds which inhibit the virulence machinery of *Pseudomonas aeruginosa*, to compounds for use for preventing and/or treating a pathogenic infection caused by *Pseudomonas aeruginosa* and also to pharmaceutical compositions for preventing and/or treating a pathogenic infection caused by *Pseudomonas aeruginosa*.

11 Claims, 2 Drawing Sheets

(56) References Cited

OTHER PUBLICATIONS

Cutting, Garry R., "Cystic fibrosis genetics: from molecular understanding to clinical application", Nature Reviews, Jan. 2015, vol. 16, pp. 45-56.
Dahlgren et al., "Design, Synthesis, and Multivariate Quantitative Structure-Activity Relationship of Salicylanilidess-Potent Inhibitors of Type III Secretion in Yersinia", Journal of Medicinal Chemistry, 2007, vol. 50, No. 24, pp. 6177-6188.
El-Solh et al., "Clinical outcomes of type III Pseudomonas aeruginosa bacteremian", Critical Care Medicine, 2012, vol. 40, No. 4, pp. 1157-1163.
Fletcher et al., "Monosubstituted 1,2,3-triazoles from two-step one-pot deprotection/click additions of trimethylsilylacetylene", Tetrahedron Letters, 2008, vol. 49, pp. 7030-7032.
Fletcher et al., "Multidentate 1,2,3-Triazole-Containing Chelators from Tandem Deprotection/Click Reactions of (Trimethylsilyl)alkynes and Comparison of Their Ruthenium(II) Complexes", Organometallics, 2008, vol. 27, No. 21, pp. 5430-5433.
Gi et al., "A Drug-Repositioning Screening Identifies Pentetic Acid as a Potential Therapeutic Agent for Suppressing the Elastase-Mediated Virulence of Pseudomonas aeruginosa", Antimicrobial Agents and Chemotherapy, Dec. 2014, vol. 58, No. 12, pp. 7205-7214.
Hauser, Alan R., "The type III secretion system of Pseudomonas aeruginosa: infection by injection", Nature Reviews, Sep. 2009, vol. 7, pp. 654-665.
Hu et al., "In Situ 'Click' Assembly of Small Molecule Matrix Metalloprotease Inhibitors Containing Zinc-Chelating Groups" Organic Letters, 2008, vol. 10, No. 24, pp. 5529-5531.
Izoré et al., "Biogenesis, Regulation, and Targeting of the Type III Secretion System", Structure, May 11, 2011, vol. 19, pp. 603-612.
Kalanuria et al., "Ventilator-associated pneumonia in the ICU", Critical Care, 2014, vol. 18, No. 208. (8 pages).
Kimura et al., "A small-molecule inhibitor of the bacterial type III secretion system protects against in vivo infection with Citrobacter rodentium", The Journal of Antibiotics, 2011, vol. 64, pp. 197-203.
Le Berre et al., "Relative contribution of three main virulence factors in Pseudomonas aeruginosa pneumonia", Critical Care Medicine, 2011, vol. 39, No. 9, pp. 2113-2120.
Mancini et al., "Synthesis and bioactivity of linear oligomers related to polymeric alkylpyridinium metabolites from Mediterranean sponge Reniera sarai", Organic and Biomolecular Chemistry, 2004, vol. 2, pp. 1368-1375.
Murray et al., "Pseudomonas aeruginosa chronic colonization in cystic fibrosis patients", Current Opinion in Pediatrics, 2007, vol. 19, pp. 83-88.
Obritsch et al., "Nosocomial Infections Due to Multidrug-Resistant Pseudomonas aeruginosa: Epidemiology and Treatment Options", Pharmacotherapy, 2005, vol. 25, No. 10, pp. 1353-1364.
Patel et al., "Characteristics of bloodstream infections in burn patients: An 11-year retrospective study", Burns, 2012, vol. 38, No. 5, pp. 685-690.
Peterson, Lance R., "Bad Bug, No Drugs: No Escape Revisited", Clinical Infectious Diseases, Sep. 15, 2009, vol. 49, pp. 992-993.
Plé et al., "Cochaperone Interactions in Export of the Type III Needle Component PscF of Pseudomonas aeruginosa", Journal of Bacteriology, Jul. 2010, vol. 192, No. 14, pp. 3801-3808.
Quinaud et al., "The PscE-PscF-PscG Complex Controls Type III Secretion Needle Biogenesis in Pseudomonas aeruginosa", The Journal of Biological Chemistry, Oct. 28, 2005, vol. 280, No. 43, pp. 36293-36300.
Quinaud et al., "Structure of the heterotrimeric complex that regulates type III secretion needle formation", Proceedings of the National Academy of Sciences of the United States of America, May 8, 2007, vol. 104, No. 19, pp. 7803-7808.
Rangel et al., "The Role of ExoS in Dissemination of Pseudomonas aeruginosa during Pneumonia", PLoS Pathogens, Jun. 19, 2015, vol. 11, No. 6. (27 pages).
Roy-Burman et al., "Type III Protein Secretion Is Associated with Death in Lower Respiratory and Systemic Pseudomonas aeruginosa Infections", The Journal of Infectious Diseases, Jun. 15, 2001, vol. 183, pp. 1767-1774.
Tsou et al., "Small molecules aimed at type III secretion systems to inhibit bacterial virulence", Medchemcomm, Jan. 1, 2013, vol. 4, No. 1, pp. 68-79.
Vance et al., "Role of the Type III Secreted Exoenzymes S, T, and Y in Systemic Spread of Pseudomonas aeruginosa PAO1 in Vivo", Infection and Immunity, 2005, vol. 73, No. 3, pp. 1706-1713.
International Search Report dated Oct. 4, 2016, by the European Patent Office in corresponding International Patent Application No. PCT/EP2005/066550. (6 pages).

\* cited by examiner

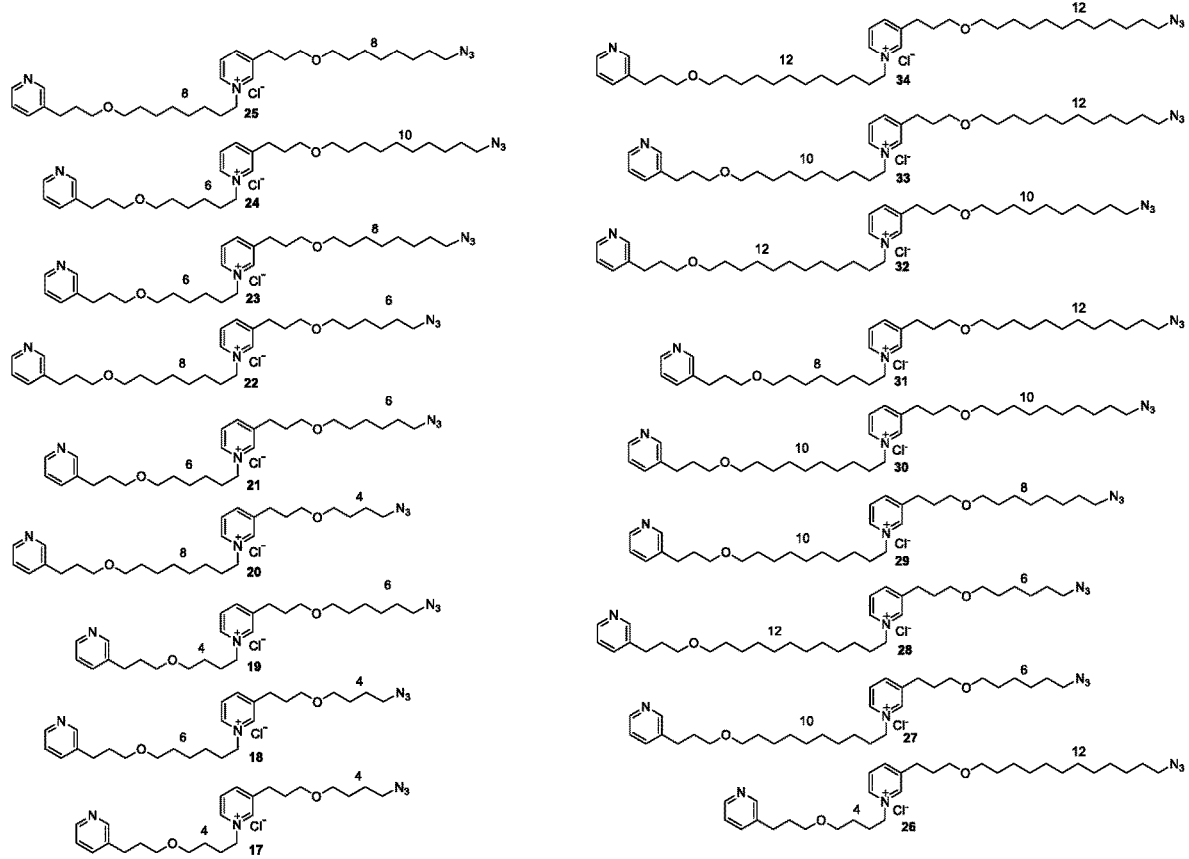
FIGURE 1: 3-APS chemical library

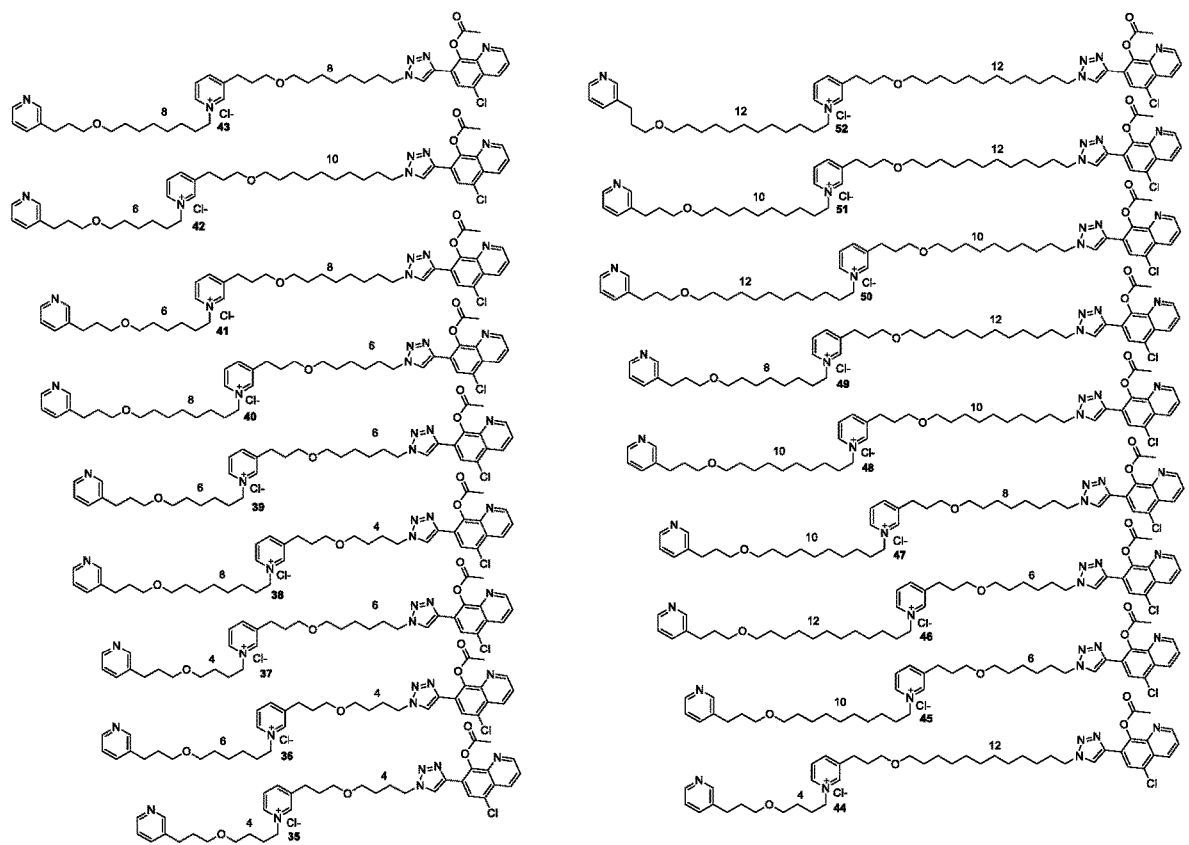
FIGURE 2: 3-APS/clioquinol hybrid chemical library.

PSEUDOMONAS AERUGINOSA INHIBITOR COMPOUNDS

CROSS-REFERENCE TO RELATED APPLICATIONS

This application is a U.S. National Stage Application pursuant to 35 U.S.C. § 371 of International Patent Application PCT/EP2016/066550, filed on Jul. 12, 2016, and published as WO 2017/009344 on Jan. 19, 2017, which claims priority to FR Patent Application 1556639, filed on Jul. 13, 2015, all of which are incorporated herein by reference in their entireties for all purposes.

The present invention relates to compounds identified by screening, in particular in an ELISA test, showing an in vitro efficacy as an inhibitor of the machinery responsible for virulence in *Pseudomonas aeruginosa*. It is the assembly of the type III secretion injectisome of these Gram-negative bacteria which is targeted by the molecules of the invention, notably the protein-protein interaction of PscE and PscG. The molecules according to the invention can be easily obtained in a few steps and allow a simple access to a wide variety of analogues. The invention is also directed to a method for identifying compounds capable of inhibiting the virulence machinery of *Pseudomonas aeruginosa*, and to a device for implementing this method of identification. The scope of application concerns the preventive and curative treatment of *Pseudomonas aeruginosa* pathologies, in particular nosocomial pathologies, and opens the door to a new antibiotic therapy which makes available compounds that render the bacteria harmless without destroying them, thereby avoiding any selection pressure which induces the appearance of a form of resistance.

*Pseudomonas aeruginosa* is a member of a family of bacterial pathogens called "ESCAPE" (*E. faecium, S. aureus, Clostridium difficile, A. baumannii, Pseudomonas aeruginosa, Enterobacteriaceae*), having the capacity to "escape" the current antibiotic treatments (L. R. Peterson. Bad bugs, no drugs: no ESCAPE revisited. *Clin. Infect. Dis.* 2009, 49, 992-993). It is omnipresent in nature and its capacity to adapt to various environments by having available a panoply of secretion effectors makes it an effective opportunistic human pathogen. Infection due to *Pseudomonas aeruginosa* can be either chronic or acute, depending on the underlying pathology or on the immune state of the individual. Linked to the increase in forms of multiple resistance to conventional antibiotics, the treatment of infections related to *Pseudomonas aeruginosa*, notably in the hospital setting, represents today a serious public health problem (F. Barbier, M. Wolff. Multi-drug resistant *Pseudomonas aeruginosa:* towards a therapeutic dead end? *Med. Sci. (Paris)* 2010, 26, 960-968). From the perspective of a new antibacterial therapy, new targets specific to the bacteria are under investigation, notably relating to the mechanism of virulence, in order to develop an alternative treatment for bacterial infections (F. Barbier, M. Wolff. Multi-drug resistant *Pseudomonas aeruginosa:* towards a therapeutic dead end? *Med. Sci. (Paris)* 2010, 26, 960-968).

During the acute infection phase, *Pseudomonas aeruginosa* uses a highly conserved type III secretion (T3S) nanomachine. Four cytotoxins, ExoS, ExoT, ExoY and ExoU, are hence injected, via the secretion needle, into the cytoplasm of the eukaryotic cell, thus weakening the host, which allows the invasion and the establishment of the infection (A. R. Hauser. The type III secretion system of *Pseudomonas aeruginosa:* infection by injection. *Nat. Rev. Microbiol.* 2009, 7, 654-665). The T3S machinery is a target of choice as shown by ongoing work which targets one of these components, PcrV, with an antibody-based therapeutic approach. In particular, high affinity antibody fragments directed against PcrV are under development by the pharmaceutical company KaloBios for the treatment of infections related to *Pseudomonas aeruginosa*.

For their virulence, and in the first stages of infection, these bacteria synthesize on the level of their bacterial membrane the T3S virulence nanomachine, also called the type III secretion injectisome, for injecting into target cells toxins, which are molecules intended to disrupt the functioning of the infected cell and ultimately to destroy it.

The T3S virulence nanomachine, or T3S virulence machinery, also referred to as T3S, consists of functionally conserved proteins which export macromolecular assembly components through the two bacterial membranes (G. R. Cornelis. The type III secretion injectisome. *Nat. Rev. Microbiol.* 2006, 4, 811-825). In *Pseudomonas aeruginosa*, as in other bacteria, T3S can be divided into three sub-assemblies: the base, the needle and the translocon, each composed of several macromolecules which interact with each other. The translocon is the most distant part of the T3S apparatus. It is composed of two hydrophobic proteins, PopB and PopD, which join to and with the membrane of the host cell. This assembly allows the passage of toxins through the plasma membrane. In the proximity of the translocon and in interaction with the secretion needle, PcrV creates the link between the two entities.

PscF is the principal component of the 80-nm-long secretion needle. The genetic inactivation of genes encoding PscE and PscG leads to strains which are non-cytotoxic to eukaryotic cells, due to the absence of T3S activity (M. Quinaud, J. Chabert, E. Faudry, E. Neumann, D. Lemaire, A. Pastor, S. Elsen, A. Dessen, I. Attree. The PscE-PscF-PscG complex controls type III secretion needle biogenesis in *Pseudomonas aeruginosa. J. Biol. Chem.* 2005, 280, 36293-36300. The resolution of the crystal structure of the PscE-PscF-PscG complex contributed greatly to the understanding of their functions (M. Quinaud, S. Ple, V. Job, C. Contreras-Martel, J. P. Simorre, I. Attree, A. Dessen. Structure of the heterotrimeric complex that regulates type III secretion needle formation. *Proc. Natl. Acad. Sci. U.S.A.* 2007, 104, 7803-7808). PscG is a protein which interacts directly with the hydrophobic part of the C-terminal helix of PscF, itself necessary to the polymerization of the needle protein. It is interesting to note that PscG interacts with PscE by a hydrophobic interaction on a surface of 1300 Å$^2$. In vitro biochemical studies carried out in parallel with in vivo experiments on *Pseudomonas aeruginosa* showed that PscE is a cochaperone of PscG, and that the absence of PscE leads to the destabilization of the PscG-PscF interaction (S. Ple, V. Job, A. Dessen, I. Attree. Cochaperone interactions in export of the type III needle component PscF of *Pseudomonas aeruginosa. J. Bacteriol.* 2010, 192, 3801-3808). Single and double point mutations introduced into the zone of interaction between PscE and PscG led to a strain of *Pseudomonas aeruginosa* with a non-cytotoxic phenotype.

In all of the studies performed on type III secretion systems, including those carried out with other pathogenic bacteria, it emerges that small synthetic molecules, as well as products of natural origin, were capable of inhibiting virulence activity in cell tests (L. K. Tsou, P. D. Dossa, H. C. Hang. Small molecules aimed at type III secretion systems to inhibit bacterial virulence. *Med. Chem. Commun.* 2013, 4, 68-79). The salicylidene acylhydrazides were among the first to show efficacy on the T3S system (WO 2006/132583). Their mode of action remains to be elucidated, although effects related to their iron chelating property, putative inhibitory effects on T3S expression, and effects leading to a decrease in secretion needle size have been put forward. The salicylanilides have been described as another family of compounds which are effective on T3S (M. K. Dahlgren, A. M. Kauppi, I.-M. Olsson, A. Linusson, M. Elofsson. Design, Synthesis, and Multivariate Quantitative Structure-Activity Relationship of Salicylanilides-Potent Inhibitors of Type III Secretion in *Yersinia*. *J. Med. Chem.* 2007, 50, 6177-6188). Other chelators have been identified by screening, such as pyridine. Other families of compounds have been discovered more recently, such as the phenoxyacetamides (WO 2010/118046 A1), the 7-methyl amine quinolines (WO 2008/115118) and the thiazolidinones (WO 2009/137133). Furthermore, natural, often complex products have also shown specific properties on T3S inhibition (K. Kimura, M. Iwatsuki, T. Nagai, A. Matsumoto, Y. Takahashi, K. Shiomi, S. Omura, A. Abe. A small-molecule inhibitor of the bacterial type III secretion system protects against in vivo infection with *Citrobacter rodentium*. *J. Antibiot.* 2011, 64, 197-203).

The presence of a functional T3S is often associated with death in patients with the respiratory and systemic infections caused by *Pseudomonas aeruginosa*. T3S appears to contribute to the development of severe pneumonia by preventing the capacity of the host to contain the bacterial infection on the level of the lungs. This not only allows *Pseudomonas aeruginosa* to persist in the lung, but it also facilitates a superinfection by other species of bacteria. Although several antibacterial agents are effective against *Pseudomonas aeruginosa*, the high mortality rates associated with *Pseudomonas aeruginosa* infections, even in hospitalized patients receiving antibiotics, reflect the need for new therapeutic agents. Moreover, the conventional bacteriostatic and bactericidal antibiotics seem inadequate to fight these infections, and the new treatment approaches, such as inhibitors of the virulence machineries of *Pseudomonas aeruginosa*, may prove useful as adjunctive therapies.

It is in this context that the inventors had the idea to develop an ELISA test for screening small molecules capable of inhibiting the interactions between the two chaperone proteins PscE and PscG.

To that end, the individual PscE and PscG proteins were purified from *E. coli*. An ELISA test was developed by fixing one of two proteins onto the surface of a solid support, such as a 96-well microtiter plate. Following washing, the second protein is added, and the interaction is detected by the specific antibodies and a colorimetric reaction, using a secondary antibody coupled to a chromogenic or fluorescent substrate. This is thus the first time that a reverse chemogenomics-type screening is carried out on the T3S system, namely that inhibitors can be identified first on the level of the protein complex (PscE-PscG chaperone) in order to then investigate the phenotypic effect on the cell (inhibition of the injectisome on the cell). Several chemical libraries were screened in order to identify the compounds capable of inhibiting the PscE-PscG interaction and thus of inhibiting the virulence machinery of *Pseudomonas aeruginosa* and ultimately of being able to prevent or treat a pathogenic infection caused by *Pseudomonas aeruginosa*.

Thus, the present invention has as an object a process for identifying molecules which inhibit the virulence machinery of *Pseudomonas aeruginosa*, a device for identifying a molecule which inhibits the virulence machinery of *Pseudomonas aeruginosa*, novel compounds which inhibit the virulence machinery of *Pseudomonas aeruginosa*, compounds for use in preventing and/or treating a pathogenic infection caused by *Pseudomonas aeruginosa*, and pharmaceutical compositions for preventing and/or treating a pathogenic infection caused by *Pseudomonas aeruginosa*.

BRIEF DESCRIPTION OF THE DRAWINGS:

FIG. 1 illustrates the chemical structures of 3-APS analogues evaluated in an ELISA test.

FIG. 2 illustrates the chemical structures of 3-APS/clioquinol analogues evaluated in an ELISA test.

DETAILED DESCRIPTION

Thus, in a first embodiment, the present invention is directed to a compound of formula (A):

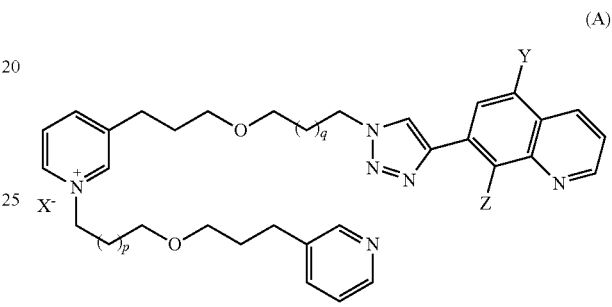

Wherein:
X is a halogen;
Y is a halogen;
Z is a hydroxy or amine group or an —$OR_1$ group wherein $R_1$ is a $C_1$-$C_4$ alkyl or a $C_1$-$C_4$ acyl;
p is an integer and 13>p≥2; and
q is an integer and 13>q≥2, with preferentially p+q<23;
on the condition that:
if p=4, then q≠8;
if p=10, then q≠4; and
if p=8, then q≠6.

Within the meaning of the present invention, the term "alkyl" or "alkyl radical" refers to a saturated linear or branched aliphatic hydrocarbon chain comprising the specified number of carbon atoms. For example, mention may be made of methyl, ethyl and propyl.

The term "acyl" or "acyl radical", abbreviated "ac", refers to a radical where a carbon atom is bonded to an oxygen by a double bond, to the structure of the molecule (A) by a single bond, and to an alkyl radical, in the case in point, in the context of the present invention, a $C_1$-$C_4$ alkyl radical.

The term "halogen" defines an atom selected from the group consisting of chlorine, fluorine, bromine and iodine.

Advantageously, X is chlorine.

Advantageously Y is chlorine.

Other pharmaceutically acceptable salts are also possible, and X can represent hydrogensulfate ($HSO_4$—), trifluoroacetic acid (TFA-), or acetic acid for example.

Advantageously $R_1$ is methyl.

Advantageously, in a second embodiment, the compound (A) according to the first embodiment is characterized by the fact that:
Z is —OH or OAc;
Y is Cl;
X is Cl; and
p and q are even numbers with preferentially 8≥p≥2 and 10≥q≥2.

In another embodiment of the present invention, the compound (A) is characterized by the fact that:

X is chlorine, Y is chlorine, $R_1$ is methyl, p=2 and q=2, 4 or 10, preferentially 4;
p=4 and q=2, 4 or 6, preferentially 4;
p=6 and q=2, 4, 6 or 10, preferentially 4; or
p=8 and q=4 or 8, preferentially 4.

In an advantageous embodiment, the compound (A) is characterized by the fact that X is chlorine, Y is chlorine, $R_1$ is methyl, p=2 and q=4.

In an advantageous embodiment, the compound (A) is characterized by the fact that X is chlorine, Y is chlorine, $R_1$ is methyl, p=4 and q=4.

In an advantageous embodiment, the compound (A) is characterized by the fact that X is chlorine, Y is chlorine, $R_1$ is methyl, p=6 and q=4.

In an advantageous embodiment, the compound (A) is characterized by the fact that X is chlorine, Y is chlorine, $R_1$ is methyl, p=4 and q=6.

In an advantageous embodiment, the compound (A) is characterized by the fact that X is chlorine, Y is chlorine, $R_1$ is methyl, p=8 and q=4.

In an advantageous embodiment, the compound (A) is characterized by the fact that X is chlorine, Y is chlorine, $R_1$ is methyl, p=8 and q=8.

In an advantageous embodiment, the compound (A) is characterized by the fact that X is chlorine, Y is chlorine, $R_1$ is methyl, p=6 and q=10.

It is also an object of the present invention to provide a process for producing a compound of formula (A) comprising the following steps:

Provide a compound of formula (B):

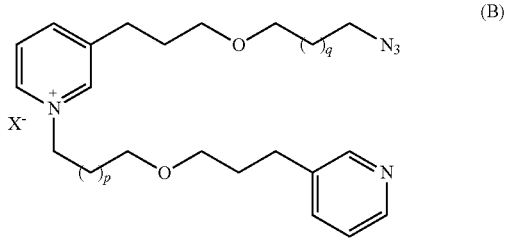

wherein X, p and q are as defined above,
which is reacted in the presence of a catalyst, preferentially copper, with the compound of formula (C):

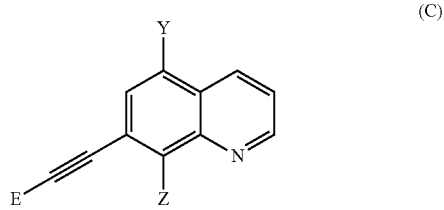

wherein Y and Z are as defined above,
and E is a leaving group.

The expression "leaving group" refers to a group that can be easily displaced by a nucleophile having higher affinity for the positively charged carbon atom to which said leaving group is attached.

In a particular embodiment, the leaving group is selected from the group consisting of trimethylsilyl, tri-isopropyl silyl (TIPS) or dimethyl alcohol for example.

It is also another object of the present invention to provide a compound of formula (D):

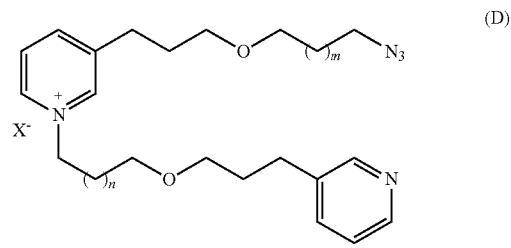

characterized in that:
X is a halogen;
m is an integer and 13>m>2; and
n is an integer and 13>n≥2, preferentially 23>m+n.

The term "halogen" defines an atom selected from the group consisting of chlorine, fluorine, bromine and iodine.

Advantageously, X is chlorine.

Other pharmaceutically acceptable salts are also possible, and X can represent hydrogensulfate ($HSO_4$—), trifluoroacetic acid (TFA-), or acetic acid for example.

In a particular embodiment, the compound of formula (D) according to the invention is characterized in that:
X is Cl;
m and n are even numbers; and/or
preferentially m+n>6.

It is also an object of the present invention to provide a compound of formula (D) according to an embodiment as illustrated above characterized in that:
m=4 and n=6 or 8, preferentially 6;
m=6 and n=8 or 10, preferentially 10;
m=8 and n=4, 6, 8, or 10, preferentially 6 or 10,
m=10 and n=4 or 10, preferentially 10.

In a particular embodiment, the compound (D) is characterized in that X is chlorine, m=4 and n=2.

In a particular embodiment, the compound (D) is characterized in that X is chlorine, m=4 and n=6.

In a particular embodiment, the compound (D) is characterized in that X is chlorine, m=6 and n=4.

In a particular embodiment, the compound (D) is characterized in that X is chlorine, m=10 and n=2.

In a particular embodiment, the compound (D) is characterized in that X is chlorine, m=4 and n=8.

In a particular embodiment, the compound (D) is characterized in that X is chlorine, m=6 and n=8.

In a particular embodiment, the compound (D) is characterized in that X is chlorine, m=8 and n=8.

In a particular embodiment, the compound (D) is characterized in that X is chlorine, m=10 and n=6.

In a particular embodiment, the compound (D) is characterized in that X is chlorine, m=10 and n=8.

In a particular embodiment, the compound (D) is characterized in that X is chlorine, m=10 and n=10.

It is also another object of the present invention to provide compounds of formula (A) and/or (D) as a medicinal product.

More particularly, the present invention concerns the compounds of formula (A) and/or (D) for use in preventing and/or treating a pathogenic infection caused by *Pseudomonas aeruginosa*.

In a particularly advantageous embodiment of the invention, the pathogenic infection treated or prevented by the compounds (A) and/or (D) according to the invention is a nosocomial infection, preferentially selected from eye infections, wound infections, in particular following a burn and/or an operation, urinary infections, in particular infections of the bladder or the urethra for example after catheterization, infections of the gastrointestinal system, lung infections in particular after bronchoscopy, meningitis in particular from inoculation, septicemia.

These compounds according to the invention have shown an efficacy as an inhibitor of the machinery responsible for virulence in *Pseudomonas aeruginosa*. These molecules target the assembly of the type III secretion injectisome of these bacteria and, more particularly, the PscE-PscG protein-protein interaction as shown here in the screening test, which is also an object of the present invention. This is the first time that synthetic compounds have been identified as inhibitors of this mechanism of action preventing the formation of the injectisome. These molecules are new and are easily obtained in a few steps (4 to 5 steps), with a simple access to a wide variety of analogues. The scope of application concerns a new antibiotic therapy which would render the bacteria harmless without inducing a bactericidal effect, thereby avoiding any selection pressure which induces the appearance of a form of resistance.

The present invention is also directed to a method for screening molecules capable of inhibiting the interactions between the two chaperones PscE and PscG and hence to inhibit the machinery responsible for virulence in *Pseudomonas aeruginosa*. To that end, first the individual PscE and PscG proteins were purified from *E. coli*. An ELISA test was developed in order to evaluate the protein-protein interaction and the inhibition thereof by the compounds tested. This test begins by fixing one of two proteins on a support, such as the material of a 96-well plate. Following washing, the second protein is added, and the interaction can be detected.

The detection of the PscE-PscG interaction and of the inhibition of this interaction can be achieved by various biochemical means at the disposal of persons skilled in the art for characterizing protein-protein interactions.

In a particular embodiment, the protein-protein interaction is evaluated by specific antibodies and by a colorimetric reaction, using a coupled secondary antibody. Several chemical libraries and 20 or so commercial natural products can be screened manually or automatically in order to identify the compounds having the desired activity. By placing the limit around 50% inhibition at a concentration of 50 μm of the molecule tested, the results of this first screening identified 17 compounds (Table 2) having an inhibition capacity making it possible to positively conclude as to their capacity to inhibit *Pseudomonas aeruginosa*. This % inhibition value can of course be placed at a lower level and is used here only as an illustrative guide value.

Thus, a tested compound may be identified as an inhibitor of the virulence machinery of *Pseudomonas aeruginosa* as of a percentage of inhibition of the PscE/PscG interaction of at least 20%, at least 30%, at least 40%, at least 50%, particularly at least 60%, more particularly at least 70%, and even more particularly at least 80%, indeed more particularly at least 90% or at least 95%.

The compounds identified by this method according to the invention are pentetic acid, clioquinol, myricetin, benserazide, gossypol, a 3-alkylpyridium 6 salt (3-APS), and hederagenin.

From the standpoint of developing structurally novel compounds, different from those already disclosed, the efforts of the inventors were dedicated to two families of compounds screened and identified as inhibitors of the PscE-PscG interaction. They are quinoline-type cation chelators such as clioquinol and pyridinium salts such as 3-alkyl pyridinium salt (3-APS). Clioquinol is one of the best inhibitors of the PscE-PscG interaction during the primary screening. 3-APSs, for their part, are constitutive elementary fragments of natural polymeric structures of marine origin having a number of biological properties.

It is also an object of the present invention to provide a process for identifying a molecule which inhibits the virulence machinery of *Pseudomonas aeruginosa* comprising a step of evaluating the capacity of said molecule to inhibit the PscE/PscG interaction.

The identification process according to the present invention envisages contacting a molecule to be tested with the PscE and PscG proteins and evaluating the capacity of said molecule to inhibit the interaction between these two proteins.

As indicated above, any method for studying and evaluating the protein-protein interaction is applicable in the context of the present invention as of the moment when it makes it possible to determine a percentage of inhibition of the PscE-PscG interaction.

In a particular embodiment of the invention, the identification process according to the invention is characterized in that the evaluation of the capacity of said molecule to inhibit the PscE/PscG interaction is carried out by an ELISA technique.

Thus, an identification process according to the present invention comprises the following steps:
a) Provide a support onto which is fixed one of the two molecules PscE or PscG,
b) Contact the support with a solution containing the molecule PscE or PscG, the molecule in solution corresponding to the one not fixed onto the support,
c) Add a solution containing the molecule to be tested
d) Wash the support
e) Add a primary antibody against the molecule not fixed onto the support, Wash the support
f) Add a secondary antibody against the primary antibody and coupled to an enzyme,
g) Wash the support
h) Add a substrate for the enzyme which generates a signal during its hydrolysis by the enzyme,
i) Quantify the signal
j) Evaluate the inhibition capacity of the molecule to be tested by comparison with a standard range.

It is also an object of the present invention to provide a device for identifying a molecule which inhibits the virulence machinery of *Pseudomonas aeruginosa* comprising a solid support onto the surface of which is fixed one of the two molecules PscE or PscG.

In a particular embodiment, the device according to the present invention is characterized in that the solid support is a microtiter plate provided with at least one well, the molecule being fixed onto the support on the level of said well.

The fixing of the molecule, PscE or PscG, can be achieved by covalent bonding or preferentially by low-energy bonding, in particular hydrophobic bonding, hydrogen bonding or Van der Walls-type bonding, i.e., also by adsorption.

Thus, the device according to the invention is characterized in that the fixing of the molecule onto the support is achieved by weak bonding.

In a particular embodiment of the device according to the present invention the surface of the solid support is hydrophobic in order to ensure the bonding, preferably by adsorption, of the molecule onto said support.

The present invention is also directed to a process for producing a device according to the present invention characterized in that:
- a1. a solid support is contacted with a solution of PscE or of PscG in order to ensure the fixing of PscE or PscG onto the surface of said support,
- b1. the solution of step a1 is removed from the support,
- c1. the support is optionally washed and/or dried, and
- d1. the screening device is recovered.

In a particular embodiment, the production of a device according to the invention is characterized in that the fixing of PscE or PscG onto the surface of the support is obtained via weak bonds of hydrophobic, hydrogen or Van der Walls type. In a particular embodiment, the production process according to the present invention is characterized in that the surface of the solid support has a hydrophobic surface treatment.

Finally, in a particular embodiment, the process for producing a device according to the invention is characterized in that the solid support is a microtiter plate comprising at least one well.

By way of particular example, a NUNC-type microtiter plate is particularly suitable.

It is also another object of the present invention to provide the use of a device according to the present invention for identifying molecules capable of inhibiting the virulence machinery of *Pseudomonas aeruginosa*.

Finally, the present invention is directed to the use of a device according to the present invention for identifying molecules capable of preventing and/or treating a pathogenic infection caused by *Pseudomonas aeruginosa*.

The present invention is directed lastly to at least one of the compounds selected from: pentetic acid, clioquinol, myricetin, benserazide, gossypol, a 3-alkylpyridium 6 salt (3-APS), and hederagenin for use in preventing and/or treating a pathogenic infection caused by *Pseudomonas aeruginosa*.

Preferentially, the compound according to the invention for use in preventing and/or treating a pathogenic infection caused by *Pseudomonas aeruginosa* is characterized in that the infection is a nosocomial infection.

In a particular embodiment, the pathogenic infection is an infection selected from eye infections, wound infections, in particular following a burn and/or a surgical operation, urinary infections, in particular infections of the bladder or the urethra for example after catheterization, infections of the gastrointestinal system, lung infections in particular after bronchoscopy, meningitis, in particular from inoculation, and septicemia.

EXAMPLE 1

Carrying Out the ELISA Test

50 μL of PscG protein at 1 μM (for screening libraries) or 2.2 μM (for screening newly synthesized molecules) is incubated in a NUNC 96-well plate for 8 h at 4° C. The wells are washed three times with 200 μL of 1× PBS/0.1% Tween20®. The wells are treated overnight at 4° C. with 200 μL of a 5% milk solution in 1× PBS/0.1% Tween20®. The solution is then discarded, and the plate is drained dry.

The test is carried out as follows:
Negative control (lowest signal level): 100 μL of buffer (25 mm Tris-HCl, 250 mM NaCl, pH 8.0);
Positive control (highest signal level): 50 μL of buffer and 50 μL of a test solution at 25 (library screening) or 3 μM (screening of analogue molecules) of the PscE protein;
Test of the inhibitors: 40 μL buffer, 50 μL of a solution at 25 μM (library screening) or 3 μM (screening of analogue molecules) of PscE protein and 10 μL of the solution containing the inhibitor to be tested.

The solutions are left for 4 h at room temperature.

The wells are washed three times with 200 μL of 1× PBS/0.1% Tween20®. The anti-PscE antibody diluted to 1:2,000 in 1× PBS/0.1% Tween20®, 50 μL, is added and the whole is left 2 h at room temperature. The wells are washed three times with 200 μL of 1× PBS/0.1% Tween20®. The HRP-conjugated anti-mouse antibody is diluted to 1:5,000 in 1× PBS/0.1% Tween20® and 50 μL is added and left for 2 h at room temperature. The wells are washed three times with 200 μL of 1× PBS/0.1% Tween20®.

The ELISA test is developed by adding 50 μL of TMB reagent followed by incubation for 15 minutes at room temperature in the dark. The reaction is stopped by adding 50 μL of 2N HCl. The plate is read at 450 nm.

Inhibition Results

TABLE 1

Molecules identified in the PscE-PscG primary screening at 50 μm

| Molecules | Name | Known properties | % inhibition PscE-PscG at 50 μm |
|---|---|---|---|
| [structure] | Pentetic acid | | 94% |

TABLE 1-continued
Molecules identified in the PscE-PscG primary screening at 50 μm
| Molecules | Name | Known properties | % inhibition PscE-PscG at 50 μm |
|---|---|---|---|
| 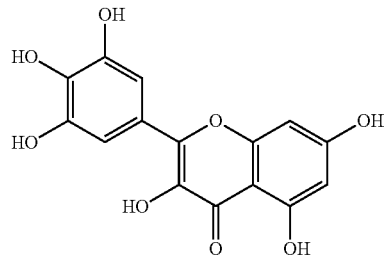 [SMILES: O=c1c(O)c(-c2cc(O)c(O)c(O)c2)oc2cc(O)cc(O)c12] | Clioquinol | Antifungal Antiprotozoal Anti-Alzheimer | 93.7% (IC$_{50}$ = 5 μm) |
| 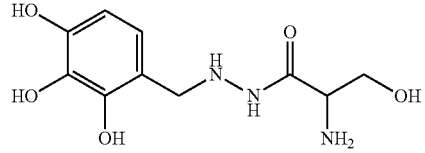 [SMILES: NC(CO)C(=O)NNCc1ccc(O)c(O)c1O] | Myricetin | Antioxidant | 80.5% |
| 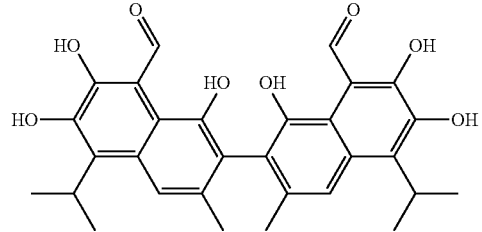 [SMILES: Cc1cc2c(C(C)C)c(O)c(O)c(C=O)c2c(O)c1-c1c(C)cc2c(C(C)C)c(O)c(O)c(C=O)c2c1O] | Benserazide | Decarboxylase inhibitor | 86.3% (IC$_{50}$ = 11 μm) |
| 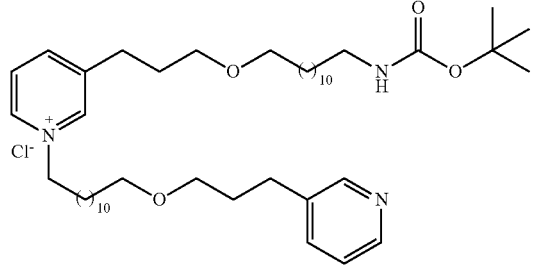 | Gossypol | | 73.9% |
| 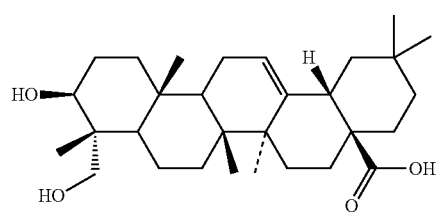 [SMILES: CC1(C)CC[C@]2(C(=O)O)CC[C@]3(C)C(=CCC4[C@@]5(C)CC[C@H](O)[C@@](C)(CO)C5CC[C@]43C)[C@@H]2C1] | 3-Alkyl pyridium 6 salts (3-APS) | | 56% |
|  | Hederagenin | | 58% |

EXAMPLE 2

Modular Synthesis of 3-APS and of 3-APS/Clioquinol Hybrids and Tests of Inhibition of the PscE-PscG Interaction New 3-APS analogues with various chain lengths, with the possibility of creating "hybrid" 3-APS/clioquinol molecules to potentiate the two clusters by synergistic effect (Scheme 1). The synthetic approach of the invention rests on the Zincke reaction. The process of the invention concerns a combinatorial synthesis strategy which makes it possible from only n fragments (in the reported example, n=5 fragments, i.e. 12a-e)+the clioquinol analogue 8, to be able to obtain potentially $2''\times2$ new analogues in a very few steps (3 to 4 steps). A Sharpless-Meldal reaction[43,44] ("click" reaction) in the presence of $K_2CO_3$ makes it possible to form 16 in a single step without preliminary deprotection of the silyl group on 8.

Scheme 1: General pathway for the modular synthesis of the 3-APS 15 and of the 3-APS/clioquinol hybrids 16.

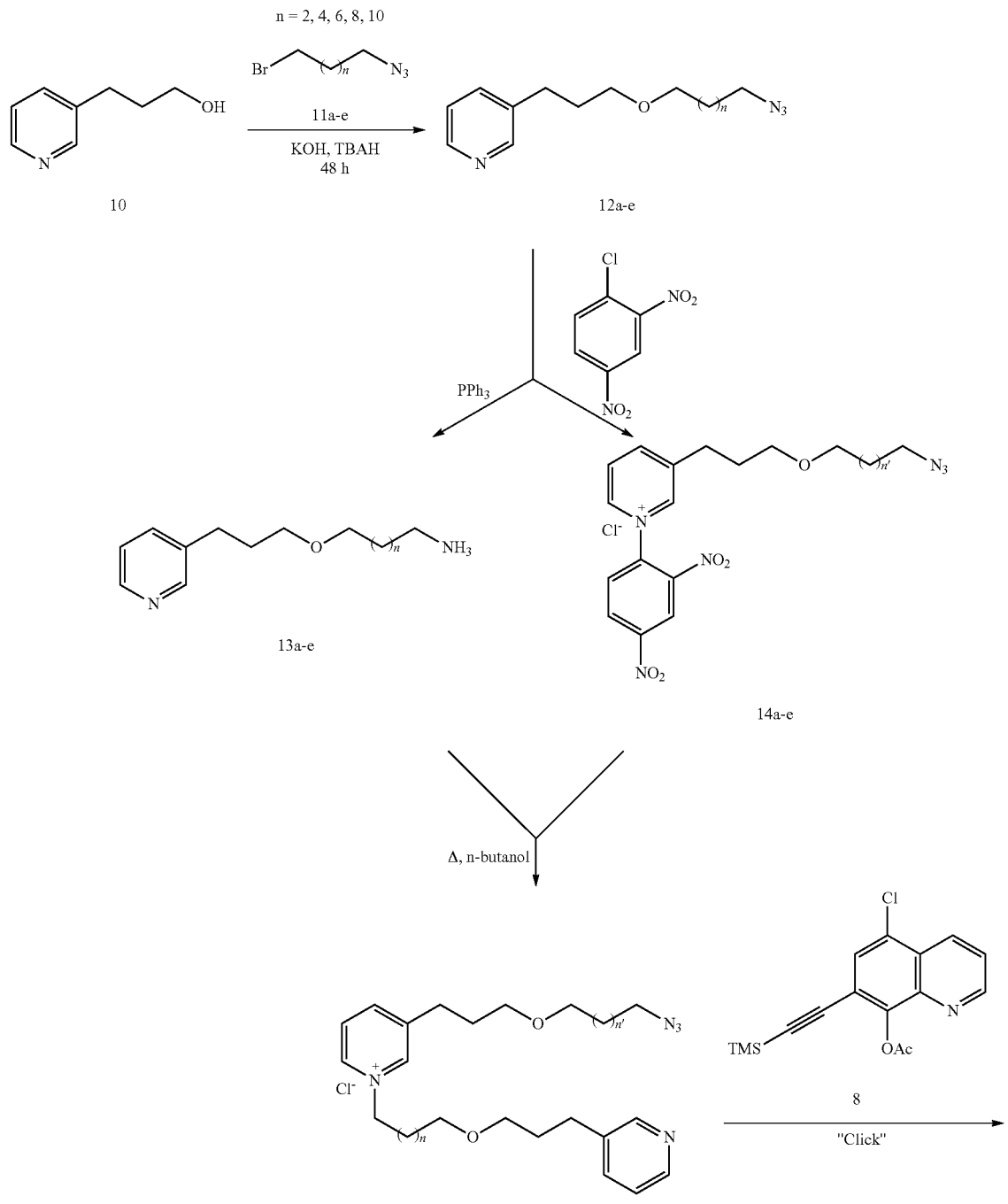

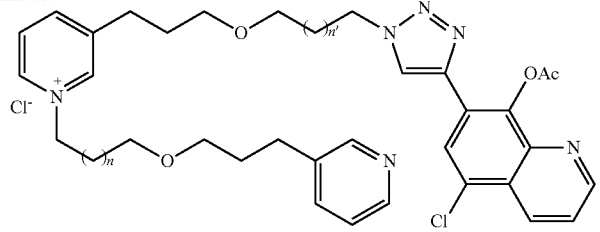

16

Results 14 3-APS analogues (e.g., FIG. 1) and the 18 3-APS/clioquinol analogues (e.g., FIG. 2) were evaluated on the ELISA test (Table 2). Of the 31 molecules tested, four molecules (22, 30, 31 and 33) in the 3-APS series and eight molecules (36, 37, 39, 40, 41, 45, 48 and 49) in the 10 hybrid 3-APS/clioquinol series showed an inhibitory effect superior to clioquinol.

TABLE 2

Result on the ELISA test of the new synthetic analogues

| Cluster | molecule | PscE-PscG at 50 μM |
|---|---|---|
| reference | clioquinol | 45.2% |
| 3-APS | 17 | no inhibition |
|  | 18 | no inhibition |
|  | 19 | 19.8% |
|  | 20 | no inhibition |
|  | 22 | 88.8% |
|  | 24 | 38.6% |
|  | 26 | 44.2% |
|  | 27 | 39.6% |
|  | 28 | 37.8% |
|  | 29 | 24% |
|  | 30 | 52.8% |
|  | 31 | 82.9% |
|  | 33 | 54.2% |
|  | 34 | 30.6% |
| 3-APS/ | 35 | 29.8% |
| clioquinol | 36 | 54.2% |
|  | 37 | 92.5% |
|  | 38 | 27.3% |
|  | 39 | 97.3% |
|  | 40 | 87.2% |
|  | 41 | 69.1% |
|  | 42 | no inhibition |
|  | 43 | 29.5% |
|  | 44 | 33.4% |
|  | 45 | 71.6% |
|  | 46 | no inhibition |
|  | 47 | no inhibition |
|  | 48 | 72.3% |
|  | 49 | 69.8% |
|  | 50 | 18.9% |
|  | 51 | 28.9% |
|  | 52 | 3.4% |

EXAMPLE 3

Preparation of the Molecules

For 1-azido-4-butane 11a: Coutrot, F., and Busseron, E., Controlling the Chair Conformation of a Mannopyranose in a Large-Amplitude [2]Rotaxane Molecular Machine, Chem.-Eur. J. 2009, 15, 5186-5190

For 1-azido-6-hexane 11 b and 1-azido-8-octane 11c: Agnew, H. D., Rohde, R. D., Millward, S. W., Nag, A., Yeo, W.-S., Hein, J. E., Pitram, S. M., Tariq, A. A., Burns, V. M., Krom, R. J., Fokin, V. V., Sharpless, K. B., and Heath, J. R., Iterative In Situ Click Chemistry Creates Antibody-like Protein-Capture Agents, Angew. Chem., Int. Ed. 2009, 48, 4944-4948.

General Procedure: Synthesis of 1-azido-10-bromodecane (11d)

A solution of 1,10-dibromodecane (9.23 g, 30.7 mmol) and $NaN_3$ (2 g, 30.7 mmol) in DMF (35 mL) is stirred at room temperature for 48 h. Ether is added (150 mL) and the organic phase is washed with water (3×150 mL). The organic phase is dried and evaporated ($MgSO_4$). The product is purified by flash chromatography (2% $CH_2Cl_2$/cyclohexane, silica gel) to give 11d in the form of a colorless oil (4.27 g, 53%).

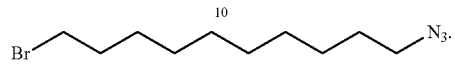

$R_f$=0.38 (cyclohexane/EtOAc 98:2); $^1$H NMR (400 MHz, $CDCl_3$) δ 1.30-1.40 (m, 10H), 1.40-1.44 (m, 2H), 1.59 (m, 2H), 1.85 (m, 2H), 3.25 (t, J=7.0 Hz, 2H), 3.40 (t, J=6.9 Hz, 2H); $^{13}$C NMR (100 MHz, $CDCl_3$) δ 26.8 ($CH_2$), 28.3 ($CH_2$), 28.8 ($CH_2$) 28.9 ($CH_2$), 29.2 ($CH_2$), 29.4 ($CH_2$), 29.5 ($CH_2$), 32.9 ($CH_2$), 34.1 ($CH_2$), 51.6 ($CH_2$).

1-azido-12-bromododecane (11e)

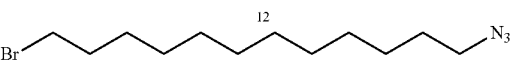 [SMILES: [N-]=[N+]=NCCCCCCCCCCCCBr]

Starting with 1,12-dibromododecane (5.05 g, 15.4 mmol), the product 11e (2.2 g, 49%) is obtained by flash chromatography (silica gel, 2% $CH_2Cl_2$/cyclohexane) in the form of a colorless oil; $R_f$=0.5 (2% $CH_2Cl_2$/cyclohexane); $^1$H NMR (400 MHz, $CDCl_3$) δ 1.25-1.33 (m, 12H), 1.59 (m, 1H), 1.85 (m, 1H), 3.25 (t, J=6.9 Hz, 1H), 3.40 (t, J=6.9 Hz, 1H); $^{13}$C NMR (100 MHz, $CDCl_3$) δ 26.9 ($CH_2$), 28.3 ($CH_2$), 28.9 ($CH_2$), 29.0 ($CH_2$), 29.3 ($CH_2$), 29.5 ($CH_2$), 29.6 (3×$CH_2$), 33.0 ($CH_2$), 34.2 ($CH_2$), 51.6 ($CH_2$).

General Procedure for Synthesizing 3-(3-(4-azidobutoxy)propyl)pyridine (12a)

To a mixture of 1-azido-4-bromobutane (1.29 g, 7.2 mmol) and 3-(3-hydroxypropyl)-pyridine (1.04 g, 7.6 mmol)

is added KOH (730 mg, 13.0 mmol) and tetrabutylammonium hydrogen sulfate (123 mg, 0.36 mmol). After mixing under argon for 48 h, CH$_2$Cl$_2$ is added and the mixture is filtered. The solvent is removed under vacuum and the product purified by flash chromatography (30% EtOAc/cyclohexane, silica gel) to give 12a in the form of a yellow oil (682 mg, 40%).

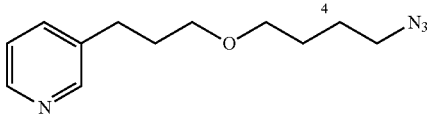 [SMILES: [N-]=[N+]=NCCCCOCCCc1cccnc1]

C$_{12}$H$_{18}$N$_4$O
M=234.15 g/mol
R$_f$=0.13 (20% EtOAc/cyclohexane); $^1$H NMR (400 MHz, CDCl$_3$) δ 1.57-1.75 (m, 4H), 1.89 (m, 2H), 2.70 (t, J=7.5 Hz, 2H), 3.31 (t, J=6.6 Hz, 2H), 3.42 (t, J=6.3 Hz, 2H), 3.44 (t, J=6.2 Hz, 2H), 7.20 (dd, J=7.7, 4.8 Hz, 1H), 7.51 (d, J=7.7 Hz, 1H), 8.43-8.45 (m, 2H); $^{13}$C NMR (100 MHz, CDCl$_3$) δ 26.0 (CH$_2$), 27.0 (CH$_2$), 29.6 (CH$_2$), 31.1 (CH$_2$), 51.4 (CH$_2$), 69.7 (CH$_2$), 70.3 (CH$_2$), 123.4 (CH), 136.0 (CH), 137.3 (C), 147.4 (CH), 150.0 (CH); LRMS (ESI+) m/z (%): 357 (70) [M+Na]$^+$; 235 (100) [M+H]$^+$.

3-(3-(6-azidohexyloxy)propyl)pyridine (12b)

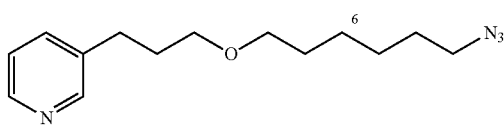

C$_{14}$H$_{22}$N$_4$O
M=262.18 g/mol
Starting with 1-azido-6-bromohexane (2.8 g, 13.4 mmol), the product 12b (2.56 g, 72%) is obtained in the form of a yellow oil.
R$_f$=0.14 (20% EtOAc/cyclohexane); $^1$H NMR (400 MHz, CDCl$_3$) δ 1.39-1.42 (m, 4H), 1.60-1.63 (m, 4H), 1.86-1.98 (m, 2H), 2.70 (t, J=7.5 Hz, 2H), 3.27 (t, J=6.9 Hz, 2H), 3.35-3.43 (m, 4H), 7.21 (dd, J=7.7, 4.8 Hz, 1H), 7.51 (dd, J=7.7, 1.6 Hz, 1H), 8.44-8.47 (m, 2H); $^{13}$C NMR (100 MHz, CDCl$_3$) δ 25.9 (CH$_2$), 26.7 (CH$_2$), 28.9 (CH$_2$), 29.6 (CH$_2$), 29.7 (CH$_2$), 31.1 (CH$_2$), 51.5 (CH$_2$), 69.6 (CH$_2$), 70.9 (CH$_2$), 123.4 (CH), 136.0 (CH), 137.3 (C), 147.4 (CH), 150.1 (CH); LRMS (ESI+) m/z (%): 285 (30) [M+Na]$^+$; 263 (100) [M+H]$^+$.

3-(3-(8-azidooctyloxy)propyl)pyridine (12c)

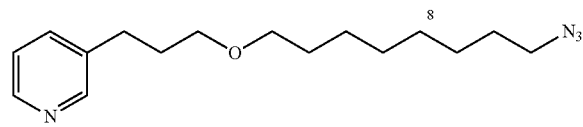 [SMILES: [N-]=[N+]=NCCCCCCCCOCCCc1cccnc1]

FW=290.21 g/mol
C$_{16}$H$_{26}$N$_4$O

Starting with 1-azido-8-bromo-octane (2.68 g, 11.4 mmol), the product 12c (2.54 g, 76.5%) is obtained in the form of a yellow oil.
R$_f$=0.18 (20% EtOAc/cyclohexane); $^1$H NMR (400 MHz, CDCl$_3$) δ 1.34-1.41 (m, 8H), 1.54-1.63 (m, 4H), 1.89 (m, 2H), 2.70 (t, J=7.4 Hz, 2H), 3.25 (t, J=6.9 Hz, 2H), 3.40 (t, J=6.6 Hz, 2H), 3.41 (t, J=6.3 Hz, 2H), 7.21 (dd, J=7.7, 4.8 Hz, 1H), 7.51 (d, J=7.7 Hz, 1H), 8.44 (dd, J=4.8, 1.6 Hz, 1H), 8.46 (d, J=1.6 Hz, 1H); $^{13}$C NMR (100 MHz, CDCl$_3$) δ 26.2 (CH$_2$), 26.8 (CH$_2$), 28.9 (CH$_2$), 29.2 (CH$_2$), 29.4 (CH$_2$), 29.6 (CH$_2$), 29.8 (CH$_2$), 31.1 (CH$_2$), 51.6 (CH$_2$), 69.6 (CH$_2$), 71.1 (CH$_2$), 123.4 (CH), 136.0 (CH), 137.3 (C), 147.4 (CH), 150.1 (CH); LRMS (ESI+) m/z (%): 313 (72) [M+Na]$^+$; 291 (100) [M+H]$^+$ 3-(3-(10-azidodecyloxy)propyl)pyridine (12d)

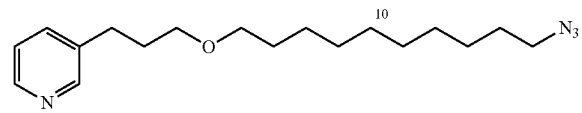

C$_{18}$H$_{30}$N$_4$O
M=318.24 g/mol
Starting with 1-azido-10-bromo-decane (3.52 g, 13.4 mmol), the product 12d (3.42 g, 80%) is obtained in the form of a yellow oil.
R$_f$=0.21 (20% EtOAc/cyclohexane); $^1$H NMR (400 MHz, CDCl$_3$) δ 1.23-1.34 (m, 12H), 1.54-1.64 (m, 4H), 1.89 (m, 2H), 2.70 (t, J=7.5 Hz, 2H), 3.25 (t, J=7.0 Hz, 2H), 3.38-3.43 (m, 4H), 7.20 (dd, J=7.5, 4.8 Hz, 1H), 7.51 (d, J=7.5 Hz, 1H), 8.44 (dd, J=4.8, 1.6 Hz, 1H), 8.46 (d, J=1.6 Hz, 1H); $^{13}$C NMR (100 MHz, CDCl$_3$) δ 26.4 (CH$_2$), 26.8 (CH$_2$), 29.0 (CH$_2$), 29.3 (CH$_2$), 29.5 (CH$_2$), 29.6 (CH$_2$), 29.6 (CH$_2$), 29.7 (CH$_2$), 29.9 (CH$_2$), 31.2 (CH$_2$), 51.6 (CH$_2$), 69.6 (CH$_2$), 71.2 (CH$_2$), 123.4 (CH), 136.0 (CH), 137.4 (C), 147.5 (CH), 150.2 (CH); LRMS (ESI+) m/z (%): 341 (55) [M+Na]$^+$; 319 (100) [M+H]$^+$.

3-(3-(12-azidododecyloxy)propyl)pyridine (12e)

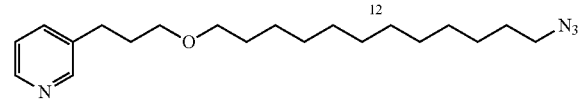 [SMILES: [N-]=[N+]=NCCCCCCCCCCCCOCCCc1cccnc1]

C$_{20}$H$_{34}$N$_4$O
MM=346
Starting with 1-azido-12-bromo-dodecane (3.71 g, 12.8 mmol), the product 12e (3.34 g, 75%) is obtained in the form of a yellow oil.
R$_f$=0.21 (20% EtOAc/cyclohexane); $^1$H NMR (400 MHz, CDCl$_3$) δ 1.23-1.40 (m, 14H), 1.54-1.63 (m, 4H), 1.89 (m, 2H), 2.71 (m, 2H), 3.25 (t, J=7.0 Hz, 2H), 3.40 (t, J=6.7 Hz, 2H), 3.41 (f, J=6.2 Hz, 2H), 7.21 (dd, J=7.8, 4.8 Hz, 1H), 7.51 (dt, J=7.8, 1.7 Hz, 1H), 8.44 (dd, J=4.8, 1.7 Hz, 1H), 8.46 (d, J=1.7 Hz, 1H); $^{13}$C NMR (100 MHz, CDCl$_3$) δ 26.0 (CH$_2$), 26.5 (CH$_2$), 28.9 (CH$_2$), 29.2 (5×CH$_2$), 29.3 (2×CH$_2$), 29.6 (CH$_2$), 30.8 (CH$_2$), 51.2 (CH$_2$), 69.1 (CH$_2$), 70.8 (CH$_2$), 123.0 (CH), 135.6 (CH), 137.0 (C), 147.0 (CH), 149.8 (CH); LRMS (ESI+) m/z (%): 347 (100) [M+H]$^+$, 319 (5).

General Procedure for Synthesizing
3-(3-(4-azidobutoxy)propyl)pyridine (13a)

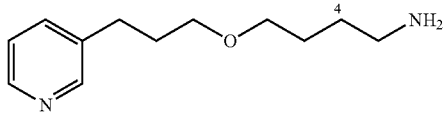

C$_{12}$H$_{20}$N$_2$O
M=208.16 g/mol

To a solution of azide 12a (390 mg, 1.67 mmol) in pyridine (12 mL) is added a portion of PPh$_3$ (828 mg, 3.2 mmol) at 0° C. After 30 min at that temperature, the mixture is stirred overnight at room temperature. After cooling to 0° C., a concentrated solution of aqueous ammonia is added (0.91 mL) and the mixture is stirred overnight at room temperature. The pyridine is removed and a 1N HCl solution (19 mL) is added. The solution is washed with ether. Solid Na$_2$CO$_3$ (2.4 g) is added by portion and the product is extracted with CH$_2$Cl$_2$. The organic solvent is dried (MgSO$_4$) and evaporated under vacuum.

The product is purified by flash chromatography (10 to 15% MeOH/CH$_2$Cl$_2$ and 15% MeOH/1%Et$_3$N/CH$_2$Cl$_2$) to obtain the product 13a (212 mg, 58%) in the form of an oil.

R$_f$=0.05 (10% MeOH/CH$_2$Cl$_2$);); $^1$H NMR (400 MHz, CDCl$_3$) δ 1.43 (m, 2H), 1.52 (m, 2H), 1.80 (m, 2H), 2.58-2.67 (m, 4H), 3.30-3.35 (m, 4H), 7.12 (dd, J=7.8, 4.8 Hz, 1H), 7.43 (d, J=7.8 Hz, 1H), 8.35 (dd, J=4.8, 1.6 Hz, 1H), 8.37 (d, J=1.6 Hz, 1H); $^{13}$C NMR (100 MHz, CDCl$_3$) δ 27.0 (CH$_2$), 29.4 (CH$_2$), 30.3 (CH$_2$), 30.9 (CH$_2$), 41.9 (CH$_2$), 69.3 (CH$_2$), 70.7 (CH$_2$), 123.2 (CH), 135.8 (CH), 137.1 (C), 147.2 (CH), 149.9 (CH); LRMS (ESI+) m/z (%): 231 (4) [M+Na]$^+$; 209 (100) [M+H]$^+$.

10-(3-(pyridin-3-yl)propoxy)hexan-1-amine (13b)

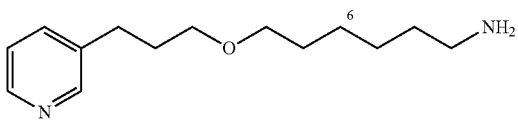

C$_{14}$H$_{24}$N$_2$O
M=236.19 g/mol

R$_f$=0.08 (15% MeOH/CH$_2$Cl$_2$); $^1$H NMR (400 MHz, CDCl$_3$) δ 1.30-1.41 (m, 4H), 1.46 (m, 2H), 1.91 (m, 2H), 2.68-2.72 (m, 4H), 3.40 (t, J=6.6 Hz, 2H), 3.41 (t, J=6.3 Hz, 2H), 7.21 (dd, J=7.7, 4.8 Hz, 1H), 7.51 (d, J=7.7 Hz, 1H), 8.44 (dd, J=4.8, 1.5 Hz, 1H), 8.46 (d, J=1.5 Hz, 1H); $^{13}$C NMR (100 MHz, CDCl$_3$) δ 26.3 (CH$_2$), 26.9 (CH$_2$), 29.7 (CH$_2$), 29.9 (CH$_2$), 31.2 (CH$_2$), 33.9 (CH$_2$), 42.2 (CH$_2$), 69.5 (CH$_2$), 71.0 (CH$_2$), 123.3 (CH), 135.9 (CH), 137.2 (C), 147.4 (CH), 150.1 (CH); LRMS (ESI+) m/z (%): 259 (12) [M+Na]$^+$; 237 (100) [M+H]$^+$.

8-(3-(pyridin-3-yl)propoxy)octan-1-amine (13c)

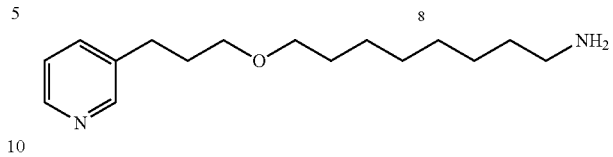

C$_{16}$H$_{28}$N$_2$O
M=264.22 g/mol

Starting with 12c (2.0 g, 6.89 mmol), the product 13c (1.32 g, 73%) is obtained in the form of a colorless oil.

R$_f$=0.05 (10% MeOH/CH$_2$Cl$_2$); $^1$H NMR (400 MHz, CDCl$_3$) δ 1.30-1.43 (m, 8H), 1.46 (m, 2H), 1.57 (m, 2H), 1.90 (m, 2H), 2.69-2.72 (m, 4H), 3.38-3.43 (m, 4H), 7.21 (dd, J=7.7, 4.8 Hz, 1H), 7.51 (d, J=7.7 Hz, 1H), 8.44 (dd, J=4.8, 1.5 Hz, 1H), 8.46 (d, J=1.5 Hz, 1H); $^{13}$C NMR (100 MHz, CDCl$_3$) δ 26.3 (CH$_2$), 27.0 (CH$_2$), 29.6 (CH$_2$), 29.7 (CH$_2$), 29.9 (CH$_2$), 31.2 (CH$_2$), 33.7 (CH$_2$), 42.3 (CH$_2$), 69.6 (CH$_2$), 71.3 (CH$_2$), 123.5 (CH), 136.1 (CH), 137.4 (C), 147.5 (CH), 150.2 (CH); LRMS (ESI+) m/z (%): 287 (7) [M+Na]$^+$; 265 (100) [M+H]$^+$.

10-(3-(pyridin-3-yl)propoxy)decan-1-amine (13d)

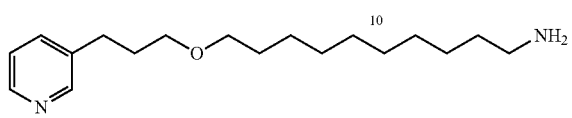

C$_{18}$H$_{32}$N$_2$O
M=292.25 g/mol

Starting with 12d (2.0 g, 6.29 mmol), the product 13d (1.58 g, 95%) is obtained in the form of a colorless oil.

R$_f$=0.10 (10% MeOH/CH$_2$Cl$_2$); $^1$H NMR (400 MHz, CDCl$_3$) δ 1.26-1.39 (m, 12H), 1.47 (m, 2H), 1.57 (m, 2H), 1.89 (m, 2H), 2.67-2.72 (m, 4H), 3.38-3.43 (m, 4H), 7.21 (dd, J=7.7, 4.8 Hz, 1H), 7.51 (d, J=7.7 Hz, 1H), 8.44 (dd, J=4.8, 1.5 Hz, 1H), 8.46 (d, J=1.5 Hz, 1H); $^{13}$C NMR (100 MHz, CDCl$_3$) δ 26.4 (CH$_2$), 27.0 (CH$_2$), 29.6 (CH$_2$), 29.7 (CH$_2$), 29.7 (CH$_2$), 29.7 (CH$_2$), 29.7 (CH$_2$), 29.7 (CH$_2$), 29.9 (CH$_2$), 31.2 (CH$_2$), 33.4 (CH$_2$), 42.2 (CH$_2$), 69.6 (CH$_2$), 71.3 (CH$_2$), 123.5 (CH), 136.1 (CH), 137.4 (C), 147.5 (CH), 150.2 (CH); LRMS (ESI+) m/z (%): 315 (4) [M+Na]$^+$; 293 (100) [M+H]$^+$.

12-(3-(pyridin-3-yl)propoxy)dodecan-1-amine (13e)

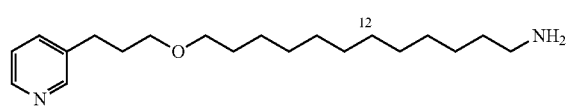 [SMILES: NCCCCCCCCCCCCOCCCc1cccnc1]

C$_{20}$H$_{36}$N$_2$O
MM=320

Starting with 12e (707 mg, 2.04 mmol), the product 13e (370 mg, 47%) is obtained in the form of a colorless oil.

R$_f$=0.13 (20% MeOH/CH$_2$Cl$_2$); $^1$H NMR (400 MHz, CDCl$_3$) δ 1.15-1.28 (m, 16H), 1.35 (m, 2H), 1.48 (m, 2H), 1.80 (m, 2H), 2.55-2.65 (m, 4H), 3.28-3.35 (m, 4H), 7.11 (dd, J=7.7, 4.8 Hz, 1H), 7.42 (d, J=7.7 Hz, 1H), 8.34 (dd, J=4.8, 1.5 Hz, 1H), 8.37 (d, J=1.5 Hz, 1H); $^{13}$C NMR (100 MHz, CDCl$_3$) δ 26.1 (CH$_2$), 26.7 (CH$_2$), 29.3 (5×CH$_2$), 29.4 (3×CH$_2$), 29.6 (CH$_2$), 30.9 (CH$_2$), 41.9 (CH$_2$), 69.2 (CH$_2$), 70.9 (CH$_2$), 123.1 (CH), 135.7 (CH), 137.1 (C), 147.1 (CH), 149.8 (CH); LRMS (ESI+) m/z (%): 343 (3) [M+Na]$^+$; 321 (100) [M+H]$^+$.

General Procedure for Synthesizing 3-(3-(4-azidobutoxy)propyl)-1-(2,4-dinitrophenyl)pyridinium chloride (14a)

The product 12a (521 mg, 2.2 mmol) and 1-chloro-2,4-dinitrobenzene (897 mg, 4.4 mmol) in ethanol (13 mL) are heated to 135° C. under stirring for 48 h. The ethanol is removed under vacuum and the product purified by flash chromatography (10% to 15% methanol/CH$_2$Cl$_2$, silica gel) to give 14a (920 mg, 86%) in the form of a brown oil.

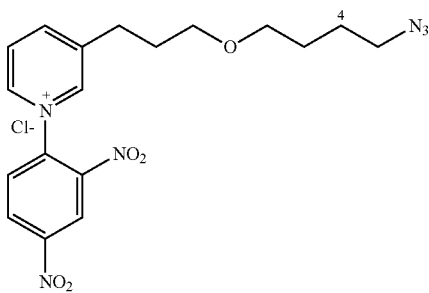

C$_{18}$H$_{21}$ClN$_6$O$_5$
MM=436.5

R$_f$=0.08 (10% MeOH/CH$_2$Cl$_2$); $^1$H NMR (400 MHz, CDCl$_3$) δ 1.60-1.68 (m, 4H), 2.09 (m, 2H), 3.12 (t, J=7.6 Hz, 2H), 3.33 (m, 2H), 3.49 (m, 2H), 3.55 (t, J=6.0 Hz, 2H), 8.34 (d, J=8.2, 6.3 Hz, 1H), 8.38 (d, J=8.7 Hz, 1H), 8.88 (d, J=8.7 Hz, 1H), 8.93 (dd, J=8.7, 2.5 Hz, 1H), 9.23 (d, J=6.3 Hz, 1H), 9.25 (d, J=2.5 Hz, 1H), 9.33 (s, 1H); $^{13}$C NMR (100 MHz, CDCl$_3$) δ 26.9 (CH$_2$), 28.0 (CH$_2$), 30.7 (CH$_2$), 31.2 (CH$_2$), 52.4 (CH$_2$), 70.3 (CH$_2$), 71.4 (CH$_2$), 123.3 (CH), 129.1 (CH), 131.4 (CH), 132.9 (CH), 140.2 (C), 144.6 (C), 144.8 (CH), 145.5 (C), 146.5 (CH), 150.2 (CH), 151.1 (C); LRMS (ESI+) m/z (%): 401 (100) [M]$^+$.

3-(3-(6-azidohexyloxy)propyl)-1-(2,4-dinitrophenyl)pyridinium chloride (14b)

Starting with 12b (1.8 g, 6.89 mmol), the product 14b (2.99 g, 93.5%) is obtained in the form of a brown oil.

R$_f$=0.09 (10% MeOH/CH$_2$Cl$_2$); $^1$H NMR (400 MHz, CDCl$_3$) δ 1.35-1.45 (m, 4H), 1.53-1.62 (m, 4H), 2.07 (m, 2H), 3.10 (t, J=7.6 Hz, 2H), 3.29 (J=6.8 Hz, 2H), 3.45 (J=6.5 Hz, 2H), 3.53 (t, J=6.0 Hz, 2H), 8.33 (d, J=8.0, 6.3 Hz, 1H), 8.37 (d, J=8.7 Hz, 1H), 8.86 (d, J=8.0 Hz, 1H), 8.92 (dd, J=8.6, 2.4 Hz, 1H), 9.22 (d, J=6.3 Hz, 1H), 9.25 (d, J=2.4 Hz, 1H), 9.32 (s, 1H); $^{13}$C NMR (100 MHz, CDCl$_3$) δ 26.9 (CH$_2$), 27.7 (CH$_2$), 29.8 (CH$_2$), 30.7 (2×CH$_2$), 31.3 (CH$_2$), 52.5 (CH$_2$), 70.3 (CH$_2$), 72.0 (CH$_2$), 123.3 (CH), 129.1 (CH), 131.3 (CH), 132.9 (CH), 140.2 (C), 144.6 (C), 144.8 (C), 145.5 (C), 146.6 (CH), 150.2 (CH), 151.1 (C); LRMS (ESI+) m/z (%): 429 (100) [M]$^+$.

3-(3-(8-azidooctyloxy)propyl)-1-(2,4-dinitrophenyl)pyridinium chloride (14c)

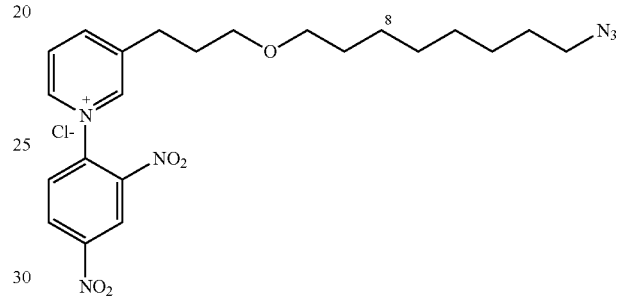

C$_{22}$H$_{29}$ClN$_6$O$_5$
M=492.2 g/mol

Starting with 12c (1.9 g, 6.89 mmol), the product 14c (2.88 g, 89%) is obtained in the form of a brown oil.

R$_f$=0.09 (10% MeOH/CH$_2$Cl$_2$); $^1$H NMR (400 MHz, CDCl$_3$) δ 1.35-1.45 (m, 8H), 1.53-1.63 (m, 4H), 2.09 (m, 2H), 3.12 (t, J=7.6 Hz, 2H), 3.30 (J=6.8 Hz, 2H), 3.46 (J=6.6 Hz, 2H), 3.54 (t, J=6.0 Hz, 2H), 8.35 (d, J=7.9, 6.3 Hz, 1H), 8.39 (d, J=8.7 Hz, 1H), 8.88 (d, J=7.9 Hz, 1H), 8.93 (dd, J=8.6, 2.4 Hz, 1H), 9.19 (d, J=6.3 Hz, 1H), 9.26 (m, 2H); $^{13}$C NMR (100 MHz, CDCl$_3$) δ 27.3 (CH$_2$), 27.9 (CH$_2$), 30.0 (CH$_2$), 30.3 (CH$_2$), 30.6 (CH$_2$), 30.8 (CH$_2$), 30.9 (CH$_2$), 31.3 (CH$_2$), 52.6 (CH$_2$), 70.3 (CH$_2$), 72.2 (CH$_2$), 123.3 (CH), 129.1 (CH), 131.3 (CH), 132.8 (CH), 140.3 (C), 144.7 (C), 144.8 (CH), 145.6 (C), 146.6 (CH), 150.3 (CH), 151.3 (C); LRMS (ESI+) m/z (%): 457 (100) [M]$^+$.

3-(3-(10-azidodecyloxy)propyl)-1-(2,4-dinitrophenyl)pyridinium chloride (14d)

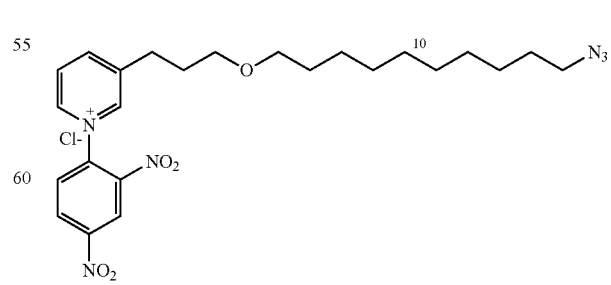

C$_{24}$H$_{33}$ClN$_6$O$_5$
M=520.5 g/mol

Starting with 12d (2.42 g, 7.6 mmol), the product 14d (3.5 g, 88.5%) is obtained in the form of a brown oil.

$R_f$=0.15 (10% MeOH/CH$_2$Cl$_2$); $^1$H NMR (400 MHz, CDCl$_3$) δ 1.30-1.40 (m, 12H), 1.52-1.62 (m, 4H), 2.07 (m, 2H), 3.09 (t, J=7.6 Hz, 2H), 3.27 (J=6.9 Hz, 2H), 3.44 (J=6.6 Hz, 2H), 3.52 (t, J=6.0 Hz, 2H), 8.31 (d, J=8.0, 6.3 Hz, 1H), 8.36 (d, J=8.7 Hz, 1H), 8.83 (d, J=8.0 Hz, 1H), 8.91 (dd, J=8.6, 2.4 Hz, 1H), 9.21 (d, J=6.3 Hz, 1H), 9.24 (d, J=2.4 Hz, 1H), 9.31 (s, 1H); $^{13}$C NMR (100 MHz, CDCl$_3$) δ 27.4 (CH$_2$), 27.9 (CH$_2$), 30.0 (CH$_2$), 30.3 (CH$_2$), 30.7 (4×CH$_2$), 30.9 (CH$_2$), 31.3 (CH$_2$), 52.5 (CH$_2$), 70.3 (CH$_2$), 72.2 (CH$_2$), 123.2 (CH), 129.1 (CH), 131.3 (CH), 132.9 (CH), 140.2 (C), 144.6 (C), 144.8 (CH), 145.5 (C), 146.5 (CH), 150.2 (CH), 151.1 (C); LRMS (ESI+) m/z (%): 485 (100) [M]$^+$ 3-(3-(12-azidododecyloxy)propyl)-1-(2,4-dinitrophenyl)pyridinium chloride (14e)

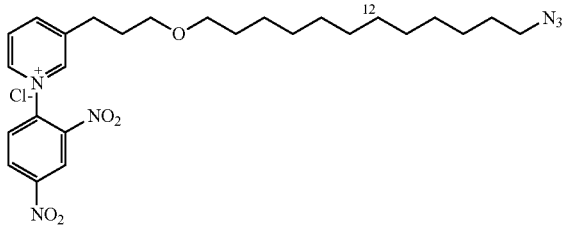

C$_{26}$H$_{37}$ClN$_6$O$_5$
MM=548.5

Starting with 12e (1.95 g, 5.64 mmol), the product 14e (2.85 g, 91%) is obtained in the form of a brown oil.

$R_f$=0.17 (10% MeOH/CH$_2$Cl$_2$); $^1$H NMR (400 MHz, CDCl$_3$) δ 1.28-1.40 (m, 16H), 1.51-1.62 (m, 4H), 2.06 (m, 2H), 3.09 (t, J=7.6 Hz, 2H), 3.28 (J=6.8 Hz, 2H), 3.43 (J=6.8 Hz, 2H), 3.51 (t, J=6.0 Hz, 2H), 8.31 (d, J=8.1, 6.3 Hz, 1H), 8.35 (d, J=8.7 Hz, 1H), 8.84 (d, J=8.1 Hz, 1H), 8.91 (dd, J=8.7, 2.4 Hz, 1H), 9.19 (d, J=6.3 Hz, 1H), 9.25 (d, J=2.4 Hz, 1H), 9.29 (s, 1H); $^{13}$C NMR (100 MHz, CDCl$_3$) δ 27.4 (CH$_2$), 27.9 (CH$_2$), 30.0 (CH$_2$), 30.4 (CH$_2$), 30.7 (4×CH$_2$), 30.8 (2×CH$_2$), 30.9 (CH$_2$), 31.3 (CH$_2$), 52.6 (CH$_2$), 70.3 (CH$_2$), 72.2 (CH$_2$), 123.2 (CH), 129.1 (CH), 131.3 (CH), 132.9 (CH), 140.3 (C), 144.7 (C), 144.8 (CH), 145.6 (C), 146.6 (CH), 150.2 (CH), 151.2 (C); LRMS (ESI+) m/z (%): 513 (100) [M]$^+$.

General Procedure for Synthesizing 3-(3-(4-azidobutoxy)propyl)-1-(4-(3-(pyridin-3-yl)propoxy)butyl)pyridinium chloride (17)

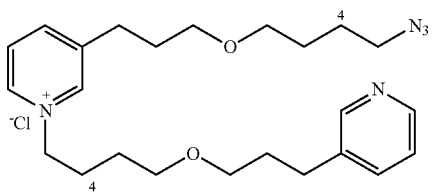

C$_{24}$H$_{36}$ClN$_5$O$_2$
MM=461.5

To the Zincke salt 14a (112 mg, 0.26 mmol) in n-butanol is added the amine 13a (70 mg, 3.1 mmol). The mixture is refluxed for 18 h. After evaporation, the product is purified by flash chromatography (7% to 10% methanol/CH$_2$Cl$_2$, silica gel) to give 17 (91 mg, 77%) in the form of a brown oil.

$R_f$=0.10 (10% MeOH/CH$_2$Cl$_2$); $^1$H NMR (400 MHz, CDCl$_3$) δ 1.58-1.7 (m, 6H), 1.89 (m, 2H), 1.99 (m, 2H), 2.09 (m, 2H), 2.73 (m, 2H), 2.97 (m, 2H), 3.30 (m, 2H), 3.41-3.51 (m, 8H), 4.66 (t, J=7.5 Hz, 2H), 7.37 (dd, J=7.7, 4.8 Hz, 1H), 7.72 (d, J=7.7 Hz, 1H), 8.03 (dd, J=7.9, 6.2 Hz, 1H), 8.37 (m, 2H), 8.47 (d, J=8.1 Hz, 1H), 8.87 (d, J=6.2 Hz, 1H), 8.96 (s, 1H); $^{13}$C NMR (100 MHz, CDCl$_3$) δ 27.0 (CH$_2$), 27.5 (CH$_2$), 28.1 (CH$_2$), 30.0 (CH$_2$), 30.5 (CH$_2$), 30.8 (CH$_2$), 31.4 (CH$_2$), 32.2 (CH$_2$), 52.4 (CH$_2$), 62.9 (CH$_2$), 70.6 (CH$_2$), 70.9 (CH$_2$), 71.1 (CH$_2$), 71.4 (CH$_2$), 125.4 (CH), 129.1 (CH), 138.6 (CH), 139.8 (C), 143.6 (CH), 145.5 (C, CH), 146.9 (CH), 147.7 (CH), 150.2 (CH); LRMS (ESI+) m/z (%): 426 (100) [M$^+$]; 398 (30).

3-(3-(4-azidobutoxy)propyl)-1-(6-(3-(pyridin-3-yl)propoxy)hexyl)pyridinium chloride (18)

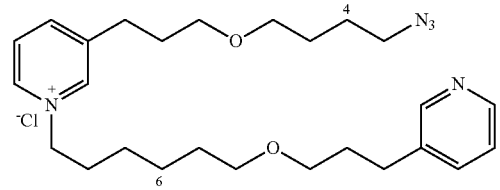

C$_{26}$H$_{40}$ClN$_5$O$_2$
MM=489.5

Starting with 14a (165 mg, 0.38 mmol) and the amine 13b (115 mg, 0.49 mmol), the product 18 (138 mg, 74%) is obtained in the form of a brown oil.

$R_f$=0.17 (10% MeOH/CH$_2$Cl$_2$); $^1$H NMR (400 MHz, CDCl$_3$) δ 1.38-1.49 (m, 6H), 1.54-1.74 (m, 4H), 1.86 (m, 2H), 1.95-2.09 (m, 4H), 2.67 (m, 2H), 2.93 (m, 2H), 3.30 (m, 2H), 3.38-3.45 (m, 6H), 4.67 (t, J=7.6 Hz, 2H), 7.37 (dd, J=7.7, 5.0 Hz, 1H), 7.71 (d, J=7.7 Hz, 1H), 8.05 (dd, J=7.8, 6.2 Hz, 1H), 8.34-8.41 (m, 2H), 8.49 (d, J=8.1 Hz, 1H), 8.93 (d, J=6.2 Hz, 1H), 9.02 (s, 1H); $^{13}$C NMR (100 MHz, CDCl$_3$) δ 26.9 (CH$_2$), 27.0 (CH$_2$), 27.1 (CH$_2$), 28.1 (CH$_2$), 30.4 (CH$_2$), 30.6 (CH$_2$), 30.7 (CH$_2$) 31.4 (CH$_2$), 32.2 (CH$_2$), 32.6 (CH$_2$), 52.4 (CH$_2$), 62.9 (CH$_2$) 70.6 (2×CH$_2$), 71.3 (CH$_2$), 71.7 (CH$_2$), 125.3 (CH), 129.0 (CH), 138.5 (CH), 139.7 (C), 143.5 (CH), 145.4 (CH), 145.5 (C), 146.8 (CH), 147.6 (CH), 150.2 (CH); LRMS (ESI+) m/z (%): 454 (100) [M$^+$], 426 (45).

3-(3-(6-azidohexyloxy)propyl)-1-(4-(3-(pyridin-3-yl)propoxy)butyl)pyridinium chloride (19)

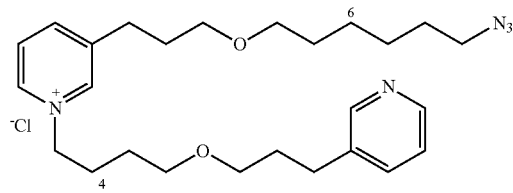

C$_{26}$H$_{40}$ClN$_5$O$_2$
MM=489.5

Starting with 13b (163 mg, 0.35 mmol) and the amine 12a (92 mg, 0.42 mmol), the product 19 (118 mg, 69%) is obtained in the form of a brown oil.

R$_f$=0.12 (10% MeOH/CH$_2$Cl$_2$); $^1$H NMR (400 MHz, CDCl$_3$) δ 1.30-1.43 (m, 4H), 1.49-1.61 (m, 4H), 1.66 (m, 2H), 1.89 (m, 2H), 2.00 (m, 2H), 2.12 (m, 2H), 2.73 (t, J=7.5 Hz, 2H), 2.98 (t, J=7.5 Hz, 2H), 3.27 (t, J=7.0 Hz, 2H), 3.37-3.53 (m, 8H), 4.70 (m, 2H), 7.39 (m, 1H), 7.72 (d, J=7.7 Hz, 1H), 8.05 (dd, J=7.8, 6.2 Hz, 1H), 8.33-8.41 (m, 2H), 8.49 (d, J=8.1 Hz, 1H), 8.92 (d, J=6.2 Hz, 1H), 9.01 (s, 1H); $^{13}$C NMR (100 MHz, CDCl$_3$) δ 27.0 (CH$_2$), 27.4 (CH$_2$) 27.7 (CH$_2$), 30.0 (2×CH$_2$), 30.5 (CH$_2$), 30.7 (CH$_2$), 30.8 (CH$_2$) 31.4 (CH$_2$), 32.2 (CH$_2$), 52.5 (CH$_2$), 62.9 (CH$_2$), 70.6 (CH$_2$) 70.9 (CH$_2$), 71.1 (CH$_2$), 71.9 (CH$_2$), 125.4 (CH), 129.1 (CH), 138.4 (CH), 139.8 (C), 143.5 (CH), 145.4 (CH), 145.5 (C), 146.9 (CH), 147.6 (CH), 150.1 (CH); LRMS (ESI+) m/z (%): 454 (100) [M$^+$], 426 (35).

3-(3-(4-azidobutoxy)propyl)-1-(8-(3-(pyridin-3-yl)propoxy)octyl)pyridinium chloride (20)

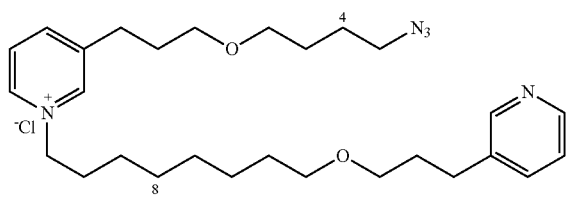

C$_{28}$H$_{44}$ClN$_5$O$_2$
MM=517.5

Starting with 13a (105 mg, 0.24 mmol) and the amine 14c (79.5 mg, 0.3 mmol), the product 20 (120 mg, 96%) is obtained in the form of a brown oil.

R$_f$=0.13 (10% MeOH/CH$_2$Cl$_2$); $^1$H NMR (400 MHz, CDCl$_3$) δ 1.30-1.46 (m, 8H), 1.51-1.71 (m, 4H), 1.87 (m, 2H), 1.95-2.06 (m, 4H), 2.73 (m, 2H), 2.97 (m, 2H), 3.30 (m, 2H), 3.37-3.46 (m, 6H), 3.49 (t, J=6.0 Hz, 2H), 4.63 (m, 2H), 7.36 (dd, J=7.7, 5.0 Hz, 1H), 7.71 (d, J=7.7 Hz, 1H), 8.02 (dd, J=7.8, 6.2 Hz, 1H), 8.34-8.39 (m, 2H), 8.47 (d, J=8.1 Hz, 1H), 8.88 (d, J=6.2 Hz, 1H), 8.97 (s, 1H); $^{13}$C NMR (100 MHz, CDCl$_3$) δ 27.0 (CH$_2$), 27.3 (CH$_2$), 27.6 (CH$_2$), 28.1 (CH$_2$), 28.7 (CH$_2$), 30.2 (CH$_2$), 30.3 (CH$_2$), 30.5 (2×CH$_2$), 30.8 (CH$_2$), 30.9 (CH$_2$), 32.2 (CH$_2$), 52.5 (CH$_2$), 63.1 (CH$_2$), 70.6 (2×CH$_2$), 71.5 (CH$_2$), 72.1 (CH$_2$), 125.4 (CH), 129.1 (CH), 138.6 (CH), 139.9 (C), 143.5 (CH), 145.5 (CH, C), 146.9 (CH), 147.6 (CH), 150.2 (CH); LRMS (ESI+) m/z (%): 482 (100) [M$^+$], 454 (42).

3-(3-(6-azidohexyloxy)propyl)-1-(6-(3-(pyridin-3-yl)propoxy)hexyl)pyridinium chloride (21)

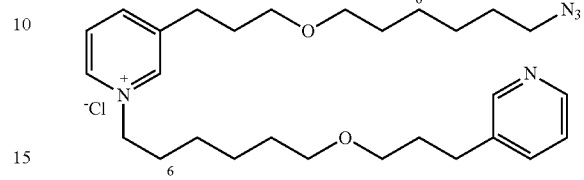

C$_{28}$H$_{44}$ClN$_5$O$_2$
MM=517.5

Starting with 14b (169 mg, 0.36 mmol) and the amine 13b (103 mg, 0.44 mmol), the product 21 (156 mg, 83%) is obtained in the form of a brown oil.

R$_f$=0.22 (15% MeOH/CH$_2$Cl$_2$); $^1$H NMR (400 MHz, CDCl$_3$) δ 1.30-1.48 (m, 8H), 1.49-1.72 (m, 6H), 1.86 (m, 2H), 1.94-2.07 (m, 4H), 2.72 (t, J=7.6 Hz, 2H), 2.97 (t, J=7.6 Hz, 2H), 3.27 (m, 2H), 3.37-3.44 (m, 6H), 3.48 (t, J=6.0 Hz, 2H), 4.63 (t, J=7.5 Hz, 2H), 7.37 (dd, J=7.6, 5.0 Hz, 1H), 7.71 (d, J=7.6 Hz, 1H), 8.02 (m, 1H), 8.32-8.39 (m, 2H), 8.47 (d, J=8.0 Hz, 1H), 8.88 (d, J=6.0 Hz, 1H), 8.97 (s, 1H); $^{13}$C NMR (100 MHz, CDCl$_3$) δ 26.9 (CH$_2$), 27.0 (CH$_2$), 27.1 (CH$_2$), 27.8 (CH$_2$), 30.0 (CH$_2$), 30.5 (CH$_2$), 30.6 (CH$_2$), 30.7 (CH$_2$), 30.8 (CH$_2$), 31.4 (CH$_2$), 32.2 (CH$_2$), 32.7 (CH$_2$), 52.5 (CH$_2$), 63.0 (CH$_2$), 70.6 (CH$_2$), 70.7 (CH$_2$), 71.8 (CH$_2$), 71.9 (CH$_2$), 125.3 (CH), 129.1 (CH), 138.5 (CH), 139.8 (C), 143.5 (CH), 145.5 (CH, C), 146.9 (CH), 147.7 (CH), 150.3 (CH); LRMS (ESI+) m/z (%): 482 (100) [M$^+$], 454 (60).

3-(3-(6-azidohexyloxy)propyl)-1-(8-(3-(pyridin-3-yl)propoxy)octyl)pyridinium chloride (22)

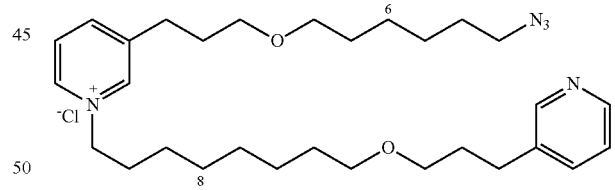

C$_{30}$H$_{48}$ClN$_5$O$_2$
MM=545.5

Starting with 14b (145 mg, 0.31 mmol) and the amine 13c (99 mg, 0.38 mmol), the product 22 (112 mg, 66%) is obtained in the form of a brown oil.

R$_f$=0.11 (10% MeOH/CH$_2$Cl$_2$); $^1$H NMR (400 MHz, CDCl$_3$) δ 1.31-1.45 (m, 12H), 1.51-1.62 (m, 6H), 1.87 (m, 2H), 1.94-2.06 (m, 4H), 2.73 (t, J=7.6 Hz, 2H), 2.96 (t, J=7.6 Hz, 2H), 3.28 (m, 2H), 3.38-3.44 (m, 6H), 3.48 (t, J=6.0 Hz, 2H), 4.60 (t, J=7.5 Hz, 2H), 7.36 (dd, J=7.6, 5.0 Hz, 1H), 7.71 (d, J=7.6 Hz, 1H), 8.01 (dd, J=7.6, 6.0 Hz, 1H), 8.33-8.40 (m, 2H), 8.46 (d, J=8.0 Hz, 1H), 8.84 (d, J=6.0 Hz, 1H), 8.93 (s, 1H); $^{13}$C NMR (100 MHz, CDCl$_3$) δ 27.0 (CH$_2$), 27.2 (CH$_2$) 27.3 (CH$_2$), 27.8 (CH$_2$), 30.0 (CH$_2$), 30.2 (CH$_2$), 30.4 (CH$_2$), 30.5 (CH$_2$), 30.7 (2×CH$_2$), 30.8 (CH$_2$), 31.4 (CH$_2$), 32.2 (CH$_2$) 32.7 (CH$_2$), 52.5 (CH$_2$), 63.0 (CH$_2$), 70.6 (2×CH$_2$), 71.8 (CH$_2$), 71.9 (CH$_2$), 125.3 (CH), 129.1 (CH), 138.5 (CH), 139.8 (C), 143.5 (CH), 145.4 (CH, C), 146.8 (CH), 147.7 (CH), 150.2 (CH); LRMS (ESI+) m/z (%): 510 (100) [M$^+$]; 482 (30); HRMS (ESI+): calcd for C$_{30}$H$_{48}$N$_5$O$_2$ [M$^+$]: 510.3802, found: 510.3802.

3-(3-(8-azidooctyloxy)propyl)-1-(6-(3-(pyridin-3-yl)propoxy)hexyl)pyridinium chloride (23)

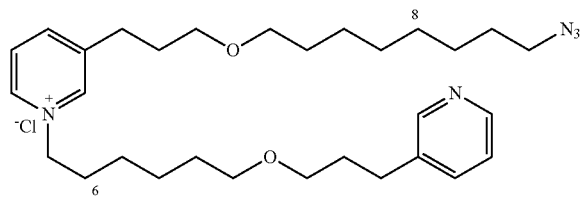

C$_{30}$H$_{48}$ClN$_5$O$_2$
MM=545.5

Starting with 14c (150 mg, 0.3 mmol) and the amine 13b (86 mg, 0.36 mmol), the product 23 (105 mg, 63%) is obtained in the form of a brown oil.

R$_f$=0.13 (10% MeOH/CH$_2$Cl$_2$); $^1$H NMR (400 MHz, CDCl$_3$) δ 1.29-1.48 (m, 12H), 1.50-1.63 (m, 6H), 1.87 (m, 2H), 1.93-2.07 (m, 4H), 2.72 (t, J=7.6 Hz, 2H), 2.96 (t, J=7.6 Hz, 2H), 3.26 (t, J=7.0 Hz, 2H), 3.38-3.45 (m, 6H), 3.48 (t, J=6.0 Hz, 2H), 4.61 (t, J=7.5 Hz, 2H), 7.36 (dd, J=7.6, 5.0 Hz, 1H), 7.71 (d, J=7.6 Hz, 1H), 8.01 (dd, J=7.8, 6.0 Hz, 1H), 8.34-8.39 (m, 2H), 8.46 (d, J=8.0 Hz, 1H), 8.86 (d, J=6.0 Hz, 1H), 8.94 (s, 1H); $^{13}$C NMR (100 MHz, CDCl$_3$) δ 26.9 (CH$_2$), 27.2 (CH$_2$), 27.3 (CH$_2$), 27.9 (CH$_2$), 30.0 (CH$_2$), 30.4 (CH$_2$), 30.5 (CH$_2$), 30.6 (CH$_2$), 30.7 (CH$_2$), 30.8 (CH$_2$), 30.9 (CH$_2$), 31.4 (CH$_2$), 32.2 (CH$_2$), 32.7 (CH$_2$), 52.6 (CH$_2$), 63.0 (CH$_2$), 70.6 (CH$_2$), 70.7 (CH$_2$), 71.8 (CH$_2$), 72.1 (CH$_2$), 125.3 (CH), 129.1 (CH), 138.5 (CH), 139.8 (C), 143.5 (CH), 145.6 (CH, C), 146.9 (CH), 147.7 (CH), 150.3 (CH); LRMS (ESI+) m/z (%): 510 (100) [M$^+$]; 482 (30).

3-(3-(10-azidodecyloxy)propyl)-1-(6-(3-(pyridin-3-yl)propoxy)hexyl)pyridinium chloride (24)

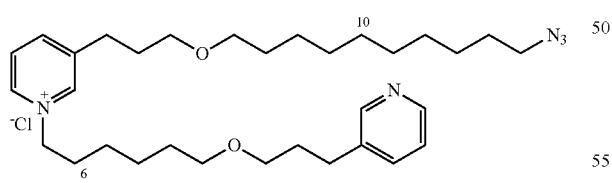

C$_{32}$H$_{52}$ClN$_5$O$_2$
MM=573.4

Starting with 14d (169 mg, 0.32 mmol) and the amine 13b (92 mg, 0.39 mmol), the product 24 (123 mg, 66%) is obtained in the form of a brown oil.

R$_f$=0.16 (10% MeOH/CH$_2$Cl$_2$); $^1$H NMR (400 MHz, CDCl$_3$) δ 1.27-1.47 (m, 16H), 1.48-1.62 (m, 6H), 1.86 (m, 2H), 1.95-2.08 (m, 4H), 2.72 (t, J=7.6 Hz, 2H), 2.97 (t, J=7.6 Hz, 2H), 3.26 (t, J=7.0 Hz, 2H), 3.37-3.45 (m, 6H), 3.48 (t, J=6.0 Hz, 2H) 4.65 (t, J=7.5 Hz, 2H), 7.37 (dd, J=7.6, 5.0 Hz, 1H), 7.71 (d, J=7.6 Hz, 1H), 8.03 (dd, J=7.8, 6.0 Hz, 1H), 8.33-8.41 (m, 2H), 8.47 (d, J=8.0 Hz, 1H), 8.90 (d, J=6.0 Hz, 1H), 8.99 (s, 1H); $^{13}$C NMR (100 MHz, CDCl$_3$) δ 26.9 (CH$_2$), 27.1 (CH$_2$), 27.4 (CH$_2$), 27.9 (CH$_2$), 30.0 (CH$_2$) 30.3 (CH$_2$), 30.5 (CH$_2$), 30.6 (CH$_2$), 30.7 (4×CH$_2$), 30.9 (CH$_2$) 31.4 (CH$_2$), 32.2 (CH$_2$), 32.6 (CH$_2$), 52.5 (CH$_2$), 63.0 (CH$_2$) 70.5 (CH$_2$), 70.6 (CH$_2$), 71.7 (CH$_2$), 72.1 (CH$_2$), 125.3 (CH), 129.0 (CH), 138.4 (CH), 139.7 (C), 143.5 (CH), 145.4 (CH, C), 146.8 (CH), 147.7 (CH), 150.2 (CH); HRMS (ESI+) m/z (%): calcd for C$_{32}$H$_{52}$N$_5$O$_2$ [M$^+$]: 538.4115, found: 538.4114.

3-(3-(8-azidooctyloxy)propyl)-1-(8-(3-(pyridin-3-yl)propoxy)octyl)pyridinium chloride (25)

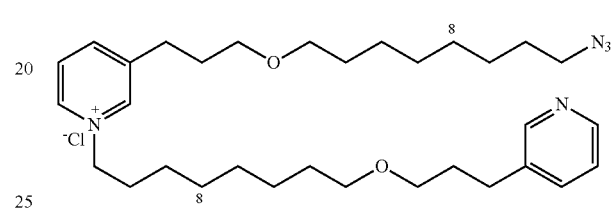

C$_{32}$H$_{52}$ClN$_5$O$_2$
MM=573.5

Starting with 14c (247 mg, 0.5 mmol) and the amine 13c (165 mg, 0.63 mmol), the product 25 (262 mg, 91%) is obtained in the form of a brown oil.

R$_f$=0.19 (10% MeOH/CH$_2$Cl$_2$); $^1$H NMR (400 MHz, CDCl$_3$) δ 1.25-1.43 (m, 16H), 1.48-1.61 (m, 6H), 1.87 (m, 2H), 1.92-2.06 (m, 4H), 2.73 (t, J=7.6 Hz, 2H), 2.96 (t, J=7.6 Hz, 2H), 3.26 (t, J=7.0 Hz, 2H), 3.37-3.44 (m, 6H), 3.48 (t, J=6.0 Hz, 2H), 4.60 (t, J=7.5 Hz, 2H), 7.36 (dd, J=7.6, 5.0 Hz, 1H), 7.71 (d, J=7.6 Hz, 1H), 8.01 (dd, J=7.8, 6.0 Hz, 1H), 8.34-8.40 (m, 2H), 8.46 (d, J=8.0 Hz, 1H), 8.85 (d, J=6.0 Hz, 1H), 8.94 (s, 1H); $^{13}$C NMR (100 MHz, CDCl$_3$) δ 27.3 (3×CH$_2$), 27.9 (CH$_2$), 30.0 (CH$_2$), 30.2 (CH$_2$), 30.3 (CH$_2$), 30.4 (CH$_2$), 30.5 (CH$_2$), 30.6 (CH$_2$), 30.8 (CH$_2$), 30.9 (2×CH$_2$), 31.4 (CH$_2$), 32.2 (CH$_2$), 32.7 (CH$_2$), 52.6 (CH$_2$), 63.1 (CH$_2$), 70.6 (2×CH$_2$), 72.0 (CH$_2$), 72.1 (CH$_2$), 125.3 (CH), 129.1 (CH), 138.6 (CH), 139.8 (C), 143.5 (CH), 145.5 (CH, C), 146.9 (CH), 147.7 (CH), 150.3 (CH); LRMS (ESI+) m/z (%): 538 (100) [M$^+$]; 510 (18).

3-(3-(12-azidododecyloxy)propyl)-1-(4-(3-(pyridin-3-yl)propoxy)butyl)pyridinium chloride (26)

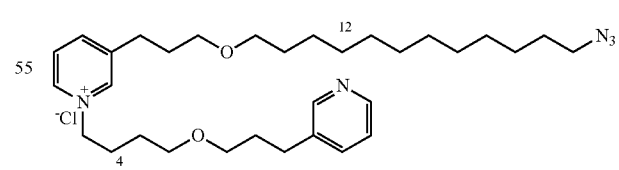

C$_{32}$H$_{52}$ClN$_5$O$_2$
MM=573.5

Starting with 14e (278 mg, 0.51 mmol) and the amine 13a (133 mg, 0.61 mmol), the product 26 (197 mg, 68%) is obtained in the form of a brown oil.

R$_f$=0.22 (10% MeOH/CH$_2$Cl$_2$); $^1$H NMR (400 MHz, CDCl$_3$) δ 1.24-1.40 (m, 16H), 1.47-1.60 (m, 4H), 1.66 (m,

2H), 1.89 (m, 2H), 2.00 (m, 2H), 2.12 (m, 2H), 2.74 (t, J=7.6 Hz, 2H), 2.98 (t, J=7.6 Hz, 2H), 3.26 (t, J=7.0 Hz, 2H), 3.40 (t, J=6.4 Hz, 2H), 3.43-3.53 (m, 6H), 4.71 (t, J=7.5 Hz, 2H), 7.40 (dd, J=7.6, 5.0 Hz, 1H), 7.75 (d, J=7.6 Hz, 1H), 8.06 (dd, J=7.8, 6.0 Hz, 1H), 8.34-8.44 (m, 2H), 8.49 (d, J=8.0 Hz, 1H), 8.94 (d, J=6.0 Hz, 1H), 9.03 (s, 1H); $^{13}$C NMR (100 MHz, CDCl$_3$) δ 27.4 (3×CH$_2$), 27.9 (CH$_2$), 29.9 (CH$_2$), 30.0 (CH$_2$), 30.4 (CH$_2$), 30.5 (CH$_2$), 30.7 (3×CH$_2$), 30.8 (2×CH$_2$), 30.9 (CH$_2$), 31.4 (CH$_2$), 32.2 (CH$_2$), 52.5 (CH$_2$), 62.8 (CH$_2$), 70.5 (CH$_2$), 70.8 (CH$_2$), 71.0 (CH$_2$), 72.1 (CH$_2$), 125.4 (CH), 129.1 (CH), 138.8 (CH), 139.9 (C), 143.5 (CH), 145.4 (CH), 145.5 (C), 146.9 (CH), 147.4 (CH), 149.9 (CH); HRMS (ESI+) m/z (%): calcd for C$_{32}$H$_{52}$N$_5$O$_2$ [M$^+$]: 538.4115, found: 538.4113.

3-(3-(6-azidohexyloxy)propyl)-1-(10-(3-(pyridin-3-yl)propoxy)decyl)pyridinium chloride (27)

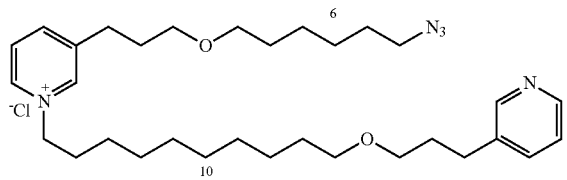

C$_{32}$H$_{52}$ClN$_5$O$_2$
MM=573.5

Starting with 14b (117.6 mg, 0.25 mmol) and the amine 13d (89 mg, 0.3 mmol), the product 27 (212 mg, 64%) is obtained in the form of a brown oil. R$_f$=0.20 (10% MeOH/CH$_2$Cl$_2$); $^1$H NMR (400 MHz, CDCl$_3$) δ 1.26-1.43 (m, 16H), 1.50-1.62 (m, 6H), 1.87 (m, 2H), 1.96-2.07 (m, 4H), 2.73 (t, J=7.6 Hz, 2H), 2.98 (t, J=7.6 Hz, 2H), 3.28 (t, J=7.0 Hz, 2H), 3.37-3.44 (m, 6H), 3.48 (t, J=6.0 Hz, 2H), 4.65 (t, J=7.5 Hz, 2H), 7.36 (dd, J=7.6, 5.0 Hz, 1H), 7.70 (d, J=7.6 Hz, 1H), 8.05 (dd, J=7.8, 6.0 Hz, 1H), 8.33-8.41 (m, 2H), 8.48 (d, J=8.0 Hz, 1H), 8.92 (d, J=6.0 Hz, 1H), 9.01 (s, 1H); $^{13}$C NMR (100 MHz, CDCl$_3$) δ 27.0 (CH$_2$), 27.3 (CH$_2$), 27.4 (CH$_2$), 27.8 (CH$_2$), 30.0 (CH$_2$), 30.2 (CH$_2$), 30.5 (CH$_2$), 30.6 (CH$_2$), 30.7 (2×CH$_2$), 30.8 (2×CH$_2$), 30.9 (CH$_2$), 31.4 (CH$_2$), 32.2 (CH$_2$), 32.7 (CH$_2$), 52.5 (CH$_2$), 63.0 (CH$_2$), 70.5 (CH$_2$), 70.6 (CH$_2$), 71.8 (CH$_2$), 72.0 (CH$_2$), 125.2 (CH), 129.0 (CH), 138.3 (CH), 139.7 (C), 143.5 (CH), 145.4 (CH), 145.5 (C), 146.8 (CH), 147.7 (CH), 150.3 (CH); HRMS (ESI+) m/z (%): calcd for C$_{32}$H$_{52}$N$_5$O$_2$ [M$^+$]: 538.4115, found: 538.4114.

3-(3-(6-azidohexyloxy)propyl)-1-(12-(3-(pyridin-3-yl)propoxy)dodecyl)pyridinium chloride (28)

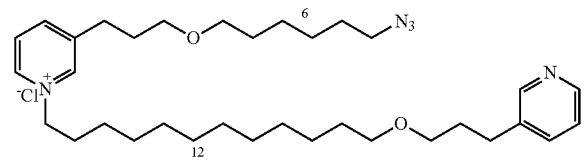

C$_{34}$H$_{56}$ClN$_5$O$_2$
MM=601.5

Starting with 14b (95 mg, 0.2 mmol) and the amine 13e (82 mg, 0.25 mmol), the product 28 (104 mg, 84%) is obtained in the form of a brown oil. R$_f$=0.19 (10% MeOH/CH$_2$Cl$_2$); $^1$H NMR (400 MHz, CDCl$_3$) δ 1.29-1.42 (m, 20H), 1.50-1.63 (m, 6H), 1.88 (m, 2H), 1.94-2.05 (m, 4H), 2.73 (t, J=7.6 Hz, 2H), 2.96 (t, J=7.6 Hz, 2H), 3.28 (t, J=7.0 Hz, 2H), 3.38-3.44 (m, 6H), 3.48 (t, J=6.0 Hz, 2H), 4.58 (t, J=7.5 Hz, 2H), 7.36 (dd, J=7.6, 5.0 Hz, 1H), 7.71 (d, J=7.6 Hz, 1H), 8.00 (dd, J=7.8, 6.0 Hz, 1H), 8.33-8.41 (m, 2H), 8.46 (d, J=8.0 Hz, 1H), 8.83 (d, J=6.0 Hz, 1H), 8.91 (s, 1H); $^{13}$C NMR (100 MHz, CDCl$_3$) δ 27.0 (CH$_2$), 27.3 (CH$_2$), 27.5 (CH$_2$), 27.8 (CH$_2$), 30.0 (CH$_2$), 30.3 (CH$_2$), 30.5 (CH$_2$), 30.6 (CH$_2$), 30.7 (3×CH$_2$), 30.8 (3×CH$_2$), 30.9 (CH$_2$), 31.4 (CH$_2$), 32.2 (CH$_2$), 32.7 (CH$_2$), 52.5 (CH$_2$), 63.1 (CH$_2$), 70.6 (CH$_2$), 70.7 (CH$_2$), 72.0 (CH$_2$), 72.1 (CH$_2$), 125.3 (CH), 129.1 (CH), 138.5 (CH), 139.8 (C), 143.4 (CH), 145.5 (C), 145.6 (CH), 146.9 (CH), 147.7 (CH), 150.3 (CH); HRMS (ESI+) m/z (%): calcd for C$_{34}$H$_{56}$N$_5$O$_2$ [M$^+$]: 566.4428, found: 566.4425.

3-(3-(8-azidooctyloxy)propyl)-1-(10-(3-(pyridin-3-yl)propoxy)decyl)pyridinium chloride (29)

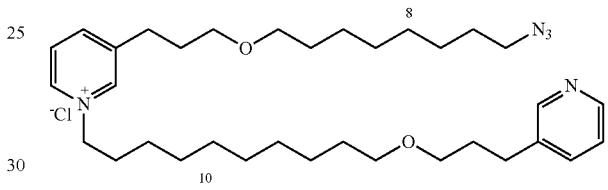

C$_{34}$H$_{56}$ClN$_5$O$_2$
MM=601.5

Starting with 14c (217 mg, 0.44 mmol) and the amine 13d (155 mg, 0.53 mmol), the product 29 (172 mg, 65%) is obtained in the form of a brown oil. R$_f$=0.20 (10% MeOH/CH$_2$Cl$_2$); $^1$H NMR (400 MHz, CDCl$_3$) δ 1.25-1.41 (m, 20H), 1.49-1.61 (m, 6H), 1.88 (m, 2H), 1.95-2.05 (m, 4H), 2.73 (t, J=7.6 Hz, 2H), 2.97 (t, J=7.6 Hz, 2H), 3.27 (t, J=7.0 Hz, 2H), 3.37-3.45 (m, 6H), 3.48 (t, J=6.0 Hz, 2H), 4.62 (t, J=7.5 Hz, 2H), 7.36 (dd, J=7.6, 5.0 Hz, 1H), 7.71 (d, J=7.6 Hz, 1H), 8.02 (dd, J=7.8, 6.0 Hz, 1H), 8.32-8.40 (m, 2H), 8.47 (d, J=8.0 Hz, 1H), 8.87 (d, J=6.0 Hz, 1H), 8.96 (s, 1H); $^{13}$C NMR (100 MHz, CDCl$_3$) δ 27.3 (2×CH$_2$), 27.5 (CH$_2$), 27.9 (CH$_2$), 30.0 (CH$_2$), 30.3 (CH$_2$), 30.4 (CH$_2$), 30.5 (CH$_2$), 30.6 (2×CH$_2$), 30.7 (2×CH$_2$), 30.8 (CH$_2$), 30.9 (2×CH$_2$), 31.4 (CH$_2$), 32.3 (CH$_2$), 32.7 (CH$_2$), 52.6 (CH$_2$), 63.1 (CH$_2$), 70.6 (2×CH$_2$), 72.1 (2×CH$_2$), 125.3 (CH), 129.1 (CH), 138.5 (CH), 139.8 (C), 143.5 (CH), 145.5 (CH, C), 146.9 (CH), 147.7 (CH), 150.3 (CH); LRMS (ESI+) m/z (%): 566 (100) [M$^+$]; 538 (24).

3-(3-(10-azidodecyloxy)propyl)-1-(10-(3-(pyridin-3-yl)propoxy)decyl)pyridinium chloride (30)

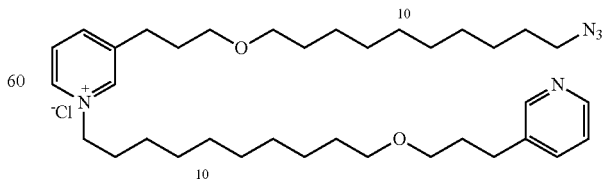

C$_{36}$H$_{60}$ClN$_5$O$_2$
MM=629.5

Starting with 14d (284 mg, 0.55 mmol) and the amine 13d (208 mg, 0.71 mmol), the product 30 (199 mg, 91%) is obtained in the form of a brown oil. $R_f$=0.12 (10% MeOH/CH$_2$Cl$_2$); $^1$H NMR (400 MHz, CDCl$_3$) δ 1.26-1.41 (m, 24H), 1.48-1.62 (m, 6H), 1.87 (m, 2H), 1.95-2.06 (m, 4H), 2.73 (t, J=7.6 Hz, 2H), 2.97 (t, J=7.6 Hz, 2H), 3.26 (t, J=7.0 Hz, 2H), 3.37-3.44 (m, 6H), 3.48 (t, J=6.0 Hz, 2H), 4.63 (t, J=7.5 Hz, 2H), 7.36 (dd, J=7.6, 5.0 Hz, 1H), 7.71 (d, J=7.6 Hz, 1H), 8.03 (dd, J=7.8, 6.0 Hz, 1H), 8.34-8.39 (m, 2H), 8.47 (d, J=8.0 Hz, 1H), 8.89 (d, J=6.0 Hz, 1H), 8.97 (s, 1H); $^{13}$C NMR (100 MHz, CDCl$_3$) δ 27.3 (CH$_2$), 27.4 (CH$_2$), 27.5 (CH$_2$), 27.9 (CH$_2$), 30.0 (CH$_2$), 30.3 (CH$_2$), 30.4 (CH$_2$), 30.5 (CH$_2$), 30.6 (CH$_2$), 30.7 (5×CH$_2$), 30.8 (CH$_2$), 30.9 (2×CH$_2$), 31.4 (CH$_2$), 32.3 (CH$_2$), 32.7 (CH$_2$), 52.6 (CH$_2$), 63.0 (CH$_2$), 70.6 (2×CH$_2$), 72.1 (2×CH$_2$), 125.3 (CH), 129.0 (CH), 138.4 (CH), 139.7 (C), 143.5 (CH), 145.4 (CH), 145.5 (C), 146.8 (CH), 147.7 (CH), 150.3 (CH); LRMS (ESI+) m/z (%): 594 (100) [M]$^+$, 566 (6). HRMS (ESI+) m/z (%): calcd for C$_{36}$H$_{60}$N$_5$O$_2$ [M$^+$]: 594.4741, found: 594.4737.

3-(3-(12-azidododecyloxy)propyl)-1-(8-(3-(pyridin-3-yl)propoxy)octyl)pyridinium chloride (31)

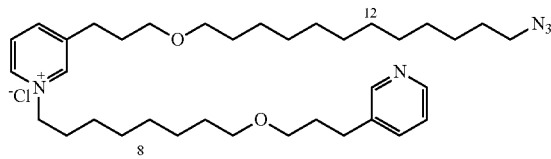

C$_{36}$H$_{60}$ClN$_5$O$_2$
MM=629.5

Starting with 14e (311 mg, 0.57 mmol) and the amine 13c (187 mg, 0.71 mmol), the product 31 (344 mg, 96%) is obtained in the form of a brown oil. $R_f$=0.28 (10% MeOH/CH$_2$Cl$_2$); $^1$H NMR (400 MHz, CDCl$_3$) δ 1.26-1.43 (m, 24H), 1.49-1.60 (m, 6H), 1.87 (m, 2H), 1.95-2.07 (m, 4H), 2.72 (t, J=7.6 Hz, 2H), 2.97 (t, J=7.6 Hz, 2H), 3.26 (t, J=7.0 Hz, 2H), 3.37-3.44 (m, 6H), 3.48 (t, J=6.0 Hz, 2H), 4.64 (t, J=7.5 Hz, 2H), 7.36 (dd, J=7.6, 5.0 Hz, 1H), 7.71 (d, J=7.6 Hz, 1H), 8.03 (dd, J=7.8, 6.0 Hz, 1H), 8.33-8.40 (m, 2H), 8.47 (d, J=8.0 Hz, 1H), 8.89 (d, J=6.0 Hz, 1H), 8.98 (s, 1H); $^{13}$C NMR (100 MHz, CDCl$_3$) δ 27.3 (2×CH$_2$), 27.4 (CH$_2$), 27.9 (CH$_2$), 30.0 (CH$_2$), 30.2 (CH$_2$), 30.4 (2×CH$_2$), 30.5 (CH$_2$), 30.7 (4×CH$_2$), 30.8 (CH$_2$), 30.9 (2×CH$_2$), 31.0 (CH$_2$), 31.4 (CH$_2$), 32.2 (CH$_2$), 32.7 (CH$_2$), 52.6 (CH$_2$), 63.0 (CH$_2$), 70.6 (2×CH$_2$), 72.0 (CH$_2$), 72.1 (CH$_2$), 125.3 (CH), 129.0 (CH), 138.4 (CH), 139.7 (C), 143.5 (CH), 145.4 (CH, C), 146.8 (CH), 147.4 (CH), 150.2 (CH); HRMS (ESI+) m/z (%): calcd for C$_{36}$H$_{48}$N$_5$O$_2$ [M$^+$]: 594.4741, found: 594.4739.

3-(3-(10-azidodecyloxy)propyl)-1-(12-(3-(pyridin-3-yl)propoxy)dodecyl)pyridinium chloride (32)

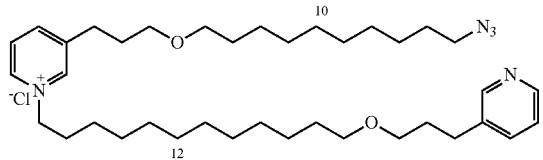

C$_{38}$H$_{64}$ClN$_5$O$_2$
MM=657.5

Starting with 14d (135 mg, 0.26 mmol) and the amine 13e (104 mg, 0.32 mmol), the product 32 (111 mg, 65%) is obtained in the form of a brown oil. $R_f$=0.25 (10% MeOH/CH$_2$Cl$_2$); $^1$H NMR (400 MHz, CDCl$_3$) δ 1.26-1.42 (m, 28H), 1.48-1.60 (m, 6H), 1.87 (m, 2H), 1.95-2.07 (m, 4H), 2.73 (t, J=7.6 Hz, 2H), 2.97 (t, J=7.6 Hz, 2H), 3.26 (t, J=7.0 Hz, 2H), 3.37-3.44 (m, 6H), 3.48 (t, J=6.0 Hz, 2H), 4.64 (t, J=7.5 Hz, 2H), 7.36 (dd, J=7.6, 5.0 Hz, 1H), 7.70 (d, J=7.6 Hz, 1H), 8.03 (dd, J=7.8, 6.0 Hz, 1H), 8.33-8.40 (m, 2H), 8.47 (d, J=8.0 Hz, 1H), 8.90 (d, J=6.0 Hz, 1H), 8.98 (s, 1H); $^{13}$C NMR (100 MHz, CDCl$_3$) δ 27.3 (CH$_2$), 27.4 (2×CH$_2$), 27.9 (CH$_2$), 30.0 (CH$_2$), 30.2 (CH$_2$), 30.4 (CH$_2$), 30.5 (CH$_2$), 30.6 (CH$_2$), 30.7 (8×CH$_2$), 30.8 (CH$_2$), 30.9 (CH$_2$), 31.4 (CH$_2$), 32.2 (CH$_2$), 32.7 (CH$_2$), 52.5 (CH$_2$), 63.0 (CH$_2$), 70.5 (CH$_2$), 70.6 (CH$_2$), 72.0 (CH$_2$), 72.1 (CH$_2$), 125.3 (CH), 129.0 (CH), 138.4 (CH), 139.7 (C), 143.5 (CH), 145.4 (CH), 145.5 (C), 146.8 (CH), 147.7 (CH), 150.3 (CH); LRMS (ESI+) m/z (%): 622 (100) [M$^+$]; 594 (12).

3-(3-(12-azidododecyloxy)propyl)-1-(10-(3-(pyridin-3-yl)propoxy)decyl)pyridinium chloride (33)

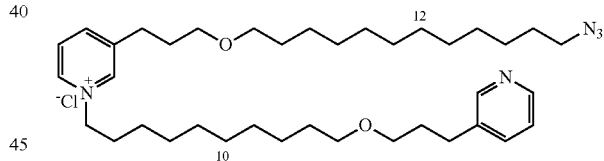

C$_{38}$H$_{64}$ClN$_5$O$_2$
MM=657.5

Starting with 14e (138 mg, 0.25 mmol) and the amine 13d (93 mg, 0.32 mmol), the product 33 (93 mg, 56%) is obtained in the form of a brown oil. $R_f$=0.14 (10% MeOH/CH$_2$Cl$_2$); $^1$H NMR (400 MHz, CDCl$_3$) δ 1.24-1.41 (m, 28H), 1.48-1.60 (m, 6H), 1.87 (m, 2H), 1.94-2.04 (m, 4H), 2.73 (t, J=7.6 Hz, 2H), 2.97 (t, J=7.6 Hz, 2H), 3.26 (t, J=7.0 Hz, 2H), 3.36-3.45 (m, 6H), 3.47 (t, J=6.0 Hz, 2H), 4.61 (t, J=7.5 Hz, 2H), 7.36 (dd, J=7.6, 5.0 Hz, 1H), 7.71 (d, J=7.6 Hz, 1H), 8.02 (dd, J=7.8, 6.0 Hz, 1H), 8.32-8.41 (m, 2H), 8.46 (d, J=8.0 Hz, 1H), 8.86 (d, J=6.0 Hz, 1H), 8.95 (s, 1H); $^{13}$C NMR (100 MHz, CDCl$_3$) δ 27.3 (CH$_2$), 27.5 (2×CH$_2$), 28.0 (CH$_2$), 30.1 (CH$_2$), 30.3 (CH$_2$), 30.4 (CH$_2$), 30.5 (CH$_2$), 30.6 (CH$_2$), 30.7 (4×CH$_2$), 30.8 (4×CH$_2$), 30.9 (CH$_2$), 31.0 (CH$_2$), 31.4 (CH$_2$), 32.3 (CH$_2$), 32.7 (CH$_2$), 52.6 (CH$_2$), 63.1 (CH$_2$), 70.6 (2×CH$_2$), 72.1 (CH$_2$), 72.2 (CH$_2$), 125.3 (CH), 129.1 (CH), 138.5 (CH), 139.8 (C), 143.5 (CH), 145.5 (CH, C), 146.9 (CH), 147.7 (CH), 150.2 (CH); LRMS (ESI+) m/z (%): 658 (100) [M$^+$]; 630 (10).

3-(3-(12-azidododecyloxy)propyl)-1-(12-(3-(pyridin-3-yl)propoxy)dodecyl)pyridinium chloride (34)

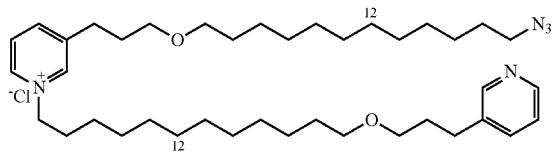

C₄₀H₆₈ClN₅O₂
MM=685.5

Starting with 14e (138 mg, 0.25 mmol) and the amine 13e (105 mg, 0.33 mmol), the product 34 (126 mg, 73%) is obtained in the form of a brown oil. $R_f$=0.14 (10% MeOH/CH₂Cl₂); ¹H NMR (400 MHz, CDCl₃) δ 1.26-1.42 (m, 32H), 1.47-1.60 (m, 6H), 1.87 (m, 2H), 1.95-2.06 (m, 4H), 2.73 (t, J=7.6 Hz, 2H), 2.97 (t, J=7.6 Hz, 2H), 3.26 (t, J=7.0 Hz, 2H), 3.36-3.44 (m, 6H), 3.48 (t, J=6.0 Hz, 2H), 4.63 (t, J=7.5 Hz, 2H), 7.36 (dd, J=7.6, 5.0 Hz, 1H), 7.71 (d, J=7.6 Hz, 1H), 8.03 (dd, J=7.8, 6.0 Hz, 1H), 8.34-8.40 (m, 2H), 8.47 (d, J=8.0 Hz, 1H), 8.89 (d, J=6.0 Hz, 1H), 8.98 (s, 1H); ¹³C NMR (100 MHz, CDCl₃) δ 27.3 (CH₂), 27.4 (2×CH₂), 27.9 (CH₂), 30.0 (CH₂), 30.2 (CH₂) 30.4 (CH₂), 30.5 (CH₂), 30.6 (CH₂), 30.7 (3×CH₂), 30.8 (6×CH₂), 30.9 (2×CH₂), 31.0 (CH₂), 31.4 (CH₂), 32.2 (CH₂), 32.7 (CH₂), 52.5 (CH₂), 63.0 (CH₂), 70.5 (CH₂), 70.6 (CH₂) 72.0 (CH₂), 72.1 (CH₂), 125.3 (CH), 129.0 (CH), 138.4 (CH), 139.7 (C), 143.5 (CH), 145.4 (CH), 145.5 (C), 146.8 (CH), 147.7 (CH), 150.2 (CH); HRMS (ESI+) m/z (%): calcd for C₄₀H₆₈N₅O₂ [M⁺]: 650.5360, found: 650.5367.

Hu, M., Li, J., and Yao, S. q. In Situ "Click" Assembly of Small Molecule Matrix Metalloprotease Inhibitors Containing Zinc-Chelating Groups, *Org. Lett.* 2008, 10, 5529-5531.

Fletcher, J. T., Walz, S. E., and Keeney, M. E. Monosubstituted 1,2,3-triazoles from two-step one-pot deprotection/click additions of trimethylsilylacetylene, *Tetrahedron Lett.* 2008, 49, 7030-7032.

Fletcher, J. T., Bumgarner, B. J., Engels, N. D., and Skoglund, D. A. Multidentate 1,2,3-Triazole-Containing Chelators from Tandem Deprotection/Click Reactions of (Trimethylsilyl)alkynes and Comparison of Their Ruthenium(II) Complexes, *Organometallics* 2008, 27, 5430-5433.

General procedure for synthesizing 3-(3-(4-(4-(8-acetoxy-5-chloroquinolin-7-yl)-1H-1,2,3-triazol-1-yl)butoxy)propyl)-1-(4-(3-(pyridin-3-yl)propoxy)butyl)pyridinium chloride (35)

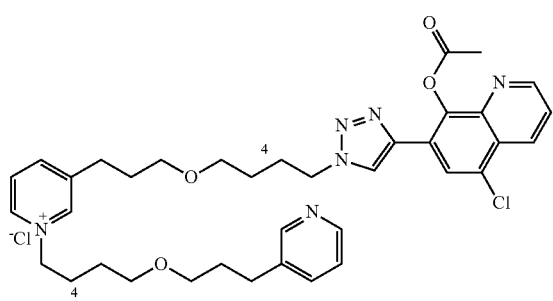

C₃₇H₄₄Cl₂N₆O₄
MM=706

To the pyridine-pyridinium salt 17 (30.4 mg, 0.066 mmol) and the TMS-protected acetylene 8 (26 mg, 0.082 mmol) in tBuOH (0.4 mL)/H₂O (0.4 mL) is added CuSO₄.5H₂O (3.3 mg, 0.013 mmol), sodium ascorbate (5.1 mg, 0.026 mmol) and K₂CO₃ (9.12 mg, 0.06 mmol). The mixture is stirred for 8 h at room temperature. EtOAc is added and the solution is filtered. After evaporation of the solvent, the product is purified by flash chromatography (7% to 10% methanol/CH₂Cl₂, silica gel) to give 35 (19 mg, 41%) in the form of a brown oil.

$R_f$=0.11 (10% MeOH/CH₂Cl₂); ¹H NMR (400 MHz, CDCl₃) δ 1.30-1.48 (m, 2H), 1.57-1.70 (m, 2H), 1.85 (m, 2H), 1.95-2.15 (m, 6H), 2.60 (s, 3H), 2.66 (t, J=7.6 Hz, 2H), 2.97 (m, 2H), 3.37-3.48 (m, 8H), 4.53 (t, J=7.0 Hz, 2H), 4.97 (t, J=7.2 Hz, 2H), 7.25 (m, 1H), 7.50-7.56 (m, 2H), 7.92 (dd, J=7.8, 6.6 Hz, 1H), 8.14 (s, 1H), 8.21 (d, J=7.8 Hz, 1H), 8.40-8.45 (m, 2H), 8.53 (s, 1H), 8.55 (dd, J=8.0, 1.1 Hz, 1H), 8.95 (dd, J=4.1, 1.1 Hz, 1H), 9.21 (d, J=5.5 Hz, 1H), 9.49 (s, 1H); ¹³C NMR (100 MHz, CDCl₃) δ 21.6 (CH₃), 26.3 (CH₂), 26.6 (CH₂), 26.7 (CH₂), 27.7 (CH₂), 29.9 (CH₂), 30.2 (CH₂), 30.9 (CH₂), 32.1 (CH₂), 50.6 (CH₂), 61.8 (CH₂), 69.4 (CH₂), 70.0 (CH₂), 70.1 (CH₂), 70.2 (CH₂), 122.6 (CH), 123.5 (CH), 123.9 (C), 125.2 (CH), 125.5 (CH), 126.9 (C), 127.8 (CH), 129.3 (C), 133.3 (CH), 135.4 (C), 136.7 (CH), 141.6 (C), 142.1 (C), 142.6 (C, CH), 144.1 (C), 144.9 (CH), 145.0 (CH), 146.9 (CH), 149.6 (CH), 151.4 (CH), 169.4 (C); LRMS (ESI+) m/z (%): 671 (2) [M⁺]; 629 (100).

3-(3-(4-(4-(8-acetoxy-5-chloroquinolin-7-yl)-1H-1,2,3-triazol-1-yl)butoxy)propyl)-1-(6-(3-(pyridin-3-yl)propoxy)hexyl)pyridinium chloride (36)

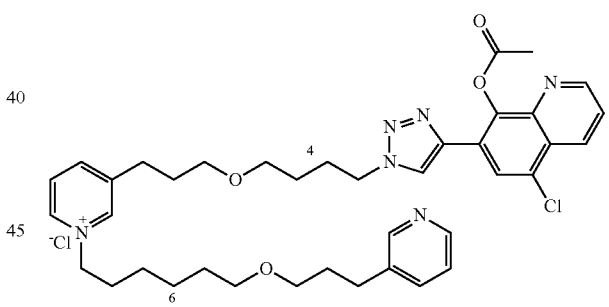

C₃₉H₄₈Cl₂N₆O₄
MM=734

Starting with the pyridine-pyridinium chloride 18 (91.5 mg, 0.18 mmol) and the TMS-protected acetylene 8 (74 mg, 0.22 mmol), the product 36 (65 mg, 47%) is obtained in the form of a brown oil. $R_f$=0.11 (10% MeOH/CH₂Cl₂); ¹H NMR (400 MHz, CDCl₃) δ 1.30-1.37 (m, 4H), 1.50 (m, 2H), 1.60 (m, 2H), 1.85 (m, 2H), 1.95-2.08 (m, 6H), 2.60 (s, 3H), 2.67 (t, J=7.6 Hz, 2H), 2.96 (t, J=7.5 Hz, 2H), 3.30-3.37 (m, 4H), 3.40-3.47 (m, 4H), 4.54 (t, J=7.0 Hz, 2H), 4.93 (t, J=7.0 Hz, 2H), 7.23 (dd, J=7.7, 4.8 Hz, 1H), 7.50-7.56 (m, 2H), 7.98 (t, J=6.7 Hz, 1H), 8.21 (s, 1H), 8.23 (d, J=8.1 Hz, 1H), 8.40-8.45 (m, 2H), 8.51 (s, 1H), 8.53 (dd, J=8.8, 1.4 Hz, 1H), 8.94 (dd, J=4.1, 1.4 Hz, 1H), 9.31 (d, J=5.3 Hz, 1H), 9.48 (s, 1H); ¹³C NMR (100 MHz, CDCl₃) δ 21.5 (CH₃), 25.8 (CH₂), 26.0 (CH₂) 26.6 (CH₂), 27.6 (CH₂), 29.4 (CH₂), 29.5 (CH₂), 29.7 (CH₂) 30.1 (CH₂), 30.9 (CH₂), 32.1 (CH₂), 50.4 (CH₂), 61.7 (CH₂) 69.3 (CH₂), 69.4 (CH₂), 70.0 (CH₂), 70.6

(CH$_2$), 122.5 (CH), 123.5 (CH), 123.6 (CH), 123.8 (C), 125.3 (CH), 126.7 (C), 127.9 (CH), 129.1 (C), 133.1 (CH), 136.4 (CH), 137.5 (C), 141.5 (C), 142.0 (C), 142.5 (C, CH), 142.7 (C), 143.8 (C), 144.6 (CH), 144.9 (CH), 146.9 (CH), 149.6 (CH), 151.3 (CH), 169.3 (C); LRMS (ESI+) m/z (%): 699 (2) [M$^+$]; 657 (100).

3-(3-(6-(4-(8-acetoxy-5-chloroquinolin-7-yl)-1H-1,2,3-triazol-1-yl)hexyloxy)propyl)-1-(4-(3-(pyridin-3-yl)propoxy)butyl)pyridinium chloride (37)

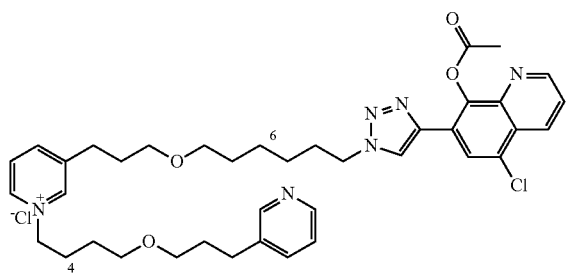

C$_{39}$H$_{48}$Cl$_2$N$_6$O$_4$
MM=734

Starting with the pyridine-pyridinium chloride 19 (89 mg, 0.18 mmol) and the TMS-protected acetylene 8 (74 mg, 0.22 mmol), the product 37 (41 mg, 31%) is obtained in the form of a brown oil. R$_f$=0.07 (10% MeOH/CH$_2$Cl$_2$); $^1$H NMR (400 MHz, CDCl$_3$) δ 1.35-1.40 (m, 4H), 1.53 (m, 2H), 1.64 (m, 2H), 1.86 (m, 2H), 1.93-2.02 (m, 4H), 2.13 (m, 2H), 2.59 (s, 3H), 2.69 (t, J=7.5 Hz, 2H), 2.96 (m, 2H), 3.35-3.47 (m, 8H), 4.49 (t, J=7.0 Hz, 2H), 5.00 (t, J=6.7 Hz, 2H), 7.32 (m, 1H), 7.51-7.60 (m, 2H), 7.97 (m, 1H), 8.08 (s, 1H), 8.21 (d, J=7.8 Hz, 1H), 8.38-8.45 (m, 2H), 8.52 (s, 1H), 8.55 (dd, J=8.5, 1.5 Hz, 1H), 8.95 (dd, J=4.2, 1.5 Hz, 1H), 9.37-9.42 (m, 2H); $^{13}$C NMR (100 MHz, CDCl$_3$) δ 21.5 (CH$_3$), 25.8 (CH$_2$), 26.3 (CH$_2$), 26.4 (CH$_2$), 29.5 (4×CH$_2$), 29.9 (CH$_2$), 30.3 (CH$_2$), 30.4 (CH$_2$), 30.9 (CH$_2$), 50.7 (CH$_2$), 61.7 (CH$_2$), 69.3 (CH$_2$), 69.9 (CH$_2$), 70.0 (CH$_2$), 70.9 (CH$_2$), 122.6 (CH), 123.2 (CH), 123.9 (C, CH), 125.4 (CH), 126.8 (C), 127.9 (CH), 129.2 (C), 133.3 (CH), 136.9 (CH), 137.6 (C), 141.6 (C), 142.1 (C), 142.5 (C), 142.9 (CH), 144.1 (C), 144.7 (CH), 144.9 (CH), 146.4 (CH), 149.1 (CH), 151.4 (CH), 169.2 (C); LRMS (ESI+) m/z (%): 699 (2) [M$^+$]; 657 (100); HRMS (ESI+) m/z (%): calcd for C$_{39}$H$_{48}$ClN$_6$O$_4$ [M$^+$]: 699.3420, found: 699.3423.

3-(3-(4-(4-(8-acetoxy-5-chloroquinolin-7-yl)-1H-1,2,3-triazol-1-yl)butoxy)propyl)-1-(8-(3-(pyridin-3-yl)propoxy)octyl)pyridinium chloride (38)

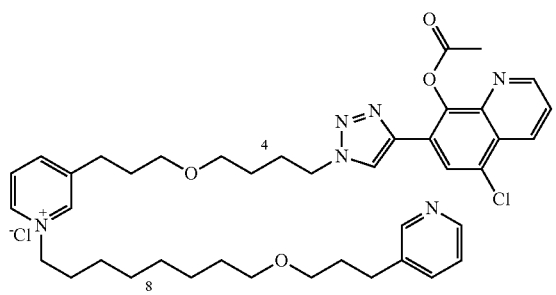

C$_{41}$H$_{52}$Cl$_2$N$_6$O$_4$
MM=762

Starting with the pyridine-pyridinium chloride 20 (86 mg, 0.17 mmol) and the TMS-protected acetylene 8 (66 mg, 0.21 mmol), the product 38 (130 mg, 42%) is obtained in the form of a brown oil. R$_f$=0.13 (10% MeOH/CH$_2$Cl$_2$); $^1$H NMR (400 MHz, CDCl$_3$) δ 1.22-1.35 (m, 8H), 1.38 (m, 2H), 1.53 (m, 2H), 1.88 (m, 2H), 1.95-2.05 (m, 6H), 2.59 (s, 3H), 2.70 (m, 2H), 2.96 (m, 2H), 3.35-3.47 (m, 8H), 4.50 (t, J=7.0 Hz, 2H), 4.95 (t, J=7.2 Hz, 2H), 7.23 (m, 1H), 7.51-7.57 (m, 2H), 7.97 (m, 1H), 8.08 (s, 1H), 8.21 (d, J=7.9 Hz, 1H), 8.38-8.45 (m, 2H), 8.52 (s, 1H), 8.55 (dd, J=8.5, 1.6 Hz, 1H), 8.95 (dd, J=4.2, 1.6 Hz, 1H), 9.32-9.37 (m, 2H); $^{13}$C NMR (100 MHz, CDCl$_3$) δ 21.5 (CH$_3$), 25.8 (CH$_2$), 26.3 (2×CH$_2$), 26.4 (CH$_2$), 29.2 (CH$_2$), 29.4 (CH$_2$), 29.5 (CH$_2$), 29.7 (CH$_2$), 29.9 (CH$_2$), 30.3 (CH$_2$), 30.4 (CH$_2$), 31.1 (CH$_2$), 32.3 (CH$_2$), 50.7 (CH$_2$), 62.1 (CH$_2$), 69.3 (CH$_2$), 69.6 (CH$_2$), 70.9 (CH$_2$), 71.2 (CH$_2$), 122.6 (CH), 123.2 (CH), 123.6 (CH), 123.9 (C), 125.5 (CH), 126.8 (C), 127.9 (CH), 129.3 (C), 133.3 (CH), 136.3 (CH), 137.6 (C), 141.6 (C), 142.1 (C), 142.6 (C), 142.9 (CH), 144.0 (C), 144.5 (CH), 144.8 (CH), 147.2 (CH), 149.6 (CH), 151.4 (CH), 169.2 (C); LRMS (ESI+) m/z (%): 727 (2) [M$^+$]; 685 (100).

3-(3-(6-(4-(8-acetoxy-5-chloroquinolin-7-yl)-1H-1,2,3-triazol-1-yl)hexyloxy)propyl)-1-(6-(3-(pyridin-3-yl)propoxy)hexyl)pyridinium chloride (39)

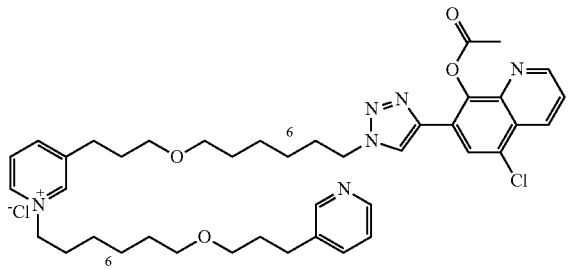

C$_{41}$H$_{52}$Cl$_2$N$_6$O$_4$
MM=762

Starting with the pyridine-pyridinium chloride 21 (59 mg, 0.11 mmol) and the TMS-protected acetylene 8 (47 mg, 0.14 mmol), the product 39 (52 mg, 60%) is obtained in the form of a brown oil. R$_f$=0.10 (10% MeOH/CH$_2$Cl$_2$); $^1$H NMR (400 MHz, CDCl$_3$) δ 1.33-1.45 (m, 10H), 1.48-1.58 (m, 4H), 1.85 (m, 2H), 1.92-2.09 (m, 4H), 2.59 (s, 3H), 2.68 (t, J=7.5 Hz, 2H), 2.96 (t, J=7.6 Hz, 2H), 3.33-3.45 (m, 8H), 4.50 (t, J=7.0 Hz, 2H), 4.96 (m, 2H), 7.24 (m, 1H), 7.49-7.58 (m, 2H), 8.00 (m, 1H), 8.11 (s, 1H), 8.23 (d, J=7.5 Hz, 1H), 8.45-8.57 (m, 4H), 8.94 (d, J=3.2 Hz, 1H), 9.40-9.45 (m, 2H); $^{13}$C NMR (100 MHz, CDCl$_3$) δ 21.5 (CH$_3$), 25.7 (CH$_2$), 25.8 (CH$_2$), 26.0 (CH$_2$), 26.3 (CH$_2$), 29.4 (CH$_2$), 29.5 (CH$_2$), 29.6 (CH$_2$), 29.8 (CH$_2$), 30.3 (CH$_2$), 30.4 (CH$_2$), 31.0 (CH$_2$), 32.2 (CH$_2$), 50.6 (CH$_2$), 61.8 (CH$_2$), 69.2 (CH$_2$), 69.5 (CH$_2$), 70.6 (CH$_2$), 70.8 (CH$_2$), 122.5 (CH), 123.2 (CH), 123.6 (CH), 123.8 (C), 125.3 (CH), 126.7 (C), 127.9 (CH), 129.2 (C), 133.2 (CH), 136.1 (CH), 137.6 (C), 141.5 (C), 142.0 (C), 142.5 (C), 142.9 (C), 143.9 (C), 144.5 (CH), 144.8 (CH), 147.2 (CH), 149.9 (CH), 151.3 (CH), 169.2 (C); HRMS (ESI+) m/z (%): calcd for C$_{41}$H$_{52}$ClN$_6$O$_4$ [M$^+$]: 727.3733, found: 727.3720.

3-(3-(6-(4-(8-acetoxy-5-chloroquinolin-7-yl)-1H-1,2,3-triazol-1-yl)hexyloxy)propyl)-1-(8-(3-(pyridin-3-yl)propoxy)octyl)pyridinium chloride (40)

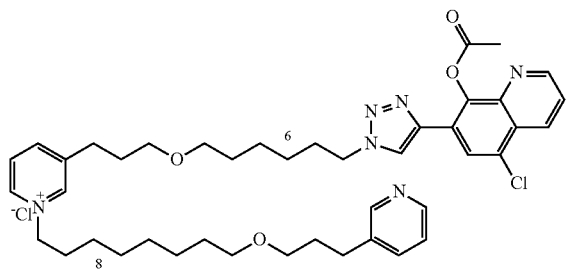

C$_{43}$H$_{56}$Cl$_2$N$_6$O$_4$
MM=790

Starting with the pyridine-pyridinium chloride 22 (85.5 mg, 0.16 mmol) and the TMS-protected acetylene 8 (62 mg, 0.20 mmol), the product 40 (73 mg, 59%) is obtained in the form of a brown oil. R$_f$=0.17 (10% MeOH/CH$_2$Cl$_2$); $^1$H NMR (400 MHz, CDCl$_3$) δ 1.20-1.44 (m, 12H), 1.47-1.56 (m, 4H), 1.87 (m, 2H), 1.91-2.09 (m, 6H), 2.59 (s, 3H), 2.69 (t, J=7.5 Hz, 2H), 2.95 (t, J=7.6 Hz, 2H), 3.32-3.45 (m, 8H), 4.50 (t, J=7.0 Hz, 2H), 4.91 (m, 2H), 7.24 (m, 1H), 7.50-7.57 (m, 2H), 7.99 (m, 1H), 8.12 (s, 1H), 8.22 (d, J=7.0 Hz, 1H), 8.38-8.57 (m, 4H), 8.94 (d, J=3.2 Hz, 1H), 9.28-9.38 (m, 2H); $^{13}$C NMR (100 MHz, CDCl$_3$) δ 21.4 (CH$_3$), 25.7 (CH$_2$), 26.1 (2×CH$_2$), 26.3 (CH$_2$), 29.1 (CH$_2$), 29.2 (CH$_2$), 29.4 (CH$_2$), 29.6 (CH$_2$), 29.7 (CH$_2$), 29.8 (CH$_2$), 30.2 (CH$_2$), 30.3 (CH$_2$), 31.0 (CH$_2$), 32.1 (CH$_2$), 50.6 (CH$_2$), 61.9 (CH$_2$), 69.2 (CH$_2$), 69.5 (CH$_2$), 70.8 (CH$_2$), 70.9 (CH$_2$), 122.5 (CH), 123.3 (CH), 123.6 (CH), 123.8 (C), 125.3 (CH), 126.7 (C), 128.0 (CH), 129.1 (C), 133.1 (CH), 136.4 (CH), 137.6 (C), 141.5 (C), 142.0 (C), 142.5 (CH), 142.8 (C), 143.8 (C), 144.3 (CH), 144.8 (CH), 147.0 (CH), 149.6 (CH), 151.3 (CH), 169.2 (C); LRMS (ESI+) m/z (%): 755 (2) [M$^+$]; 713 (100); HRMS (ESI+) m/z (%): calcd for C$_{43}$H$_{56}$ClN$_6$O$_4$ [M$^+$]: 755.4046, found: 755.4029.

3-(3-(8-(4-(8-acetoxy-5-chloroquinolin-7-yl)-1H-1,2,3-triazol-1-yl)octyloxy)propyl)-1-(6-(3-(pyridin-3-yl)propoxy)hexyl)pyridinium chloride (41)

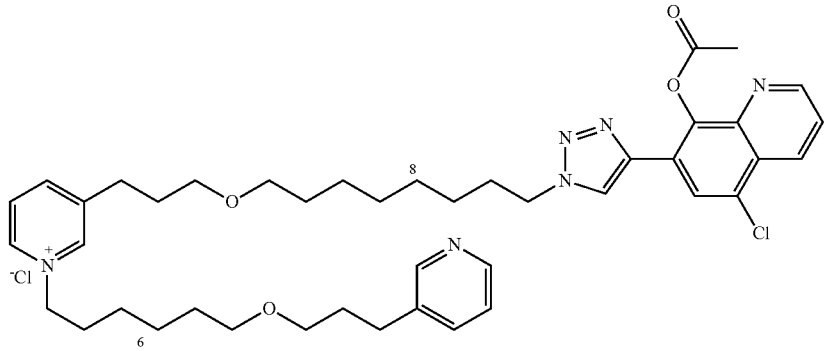

C$_{43}$H$_{56}$Cl$_2$N$_6$O$_4$
MM=790

Starting with the pyridine-pyridinium chloride 23 (98.6 mg, 0.18 mmol) and the TMS-protected acetylene 8 (71 mg, 0.22 mmol), the product 41 (62 mg, 44%) is obtained in the form of a brown oil. R$_f$=0.14 (10% MeOH/CH$_2$Cl$_2$); $^1$H NMR (400 MHz, CDCl$_3$) δ 1.22-1.44 (m, 14H), 1.45-1.57 (m, 4H), 1.86 (m, 2H), 1.90-2.09 (m, 6H), 2.57 (s, 3H), 2.70 (m, 2H), 2.95 (m, 2H), 3.30-3.45 (m, 8H), 4.46 (m, 2H), 4.92 (m, 2H), 7.37 (m, 1H), 7.48-7.62 (m, 2H), 7.98 (m, 1H), 8.02 (m, 1H), 8.20 (m, 1H), 8.48-8.57 (m, 2H), 8.94 (s, 1H), 9.25 (m, 1H), 9.34 (m, 1H); $^{13}$C NMR (100 MHz, CDCl$_3$) δ 21.5 (CH$_3$), 25.8 (CH$_2$), 26.0 (CH$_2$) 26.1 (CH$_2$), 26.5 (CH$_2$), 29.0 (CH$_2$) 29.3 (CH$_2$), 29.5 (CH$_2$) 29.7 (CH$_2$), 29.8 (2×CH$_2$), 30.3 (CH$_2$), 30.4 (CH$_2$), 31.0 (CH$_2$), 32.2 (CH$_2$), 50.7 (CH$_2$), 62.0 (CH$_2$) 69.1 (CH$_2$), 69.5 (CH$_2$) 70.6 (CH$_2$), 71.1 (CH$_2$), 122.6 (CH) 123.1 (CH), 123.8 (CH), 123.9 (C), 125.5 (CH$_2$), 126.8 (C), 128.0 (CH), 129.2 (C), 133.3 (CH), 136.3 (CH), 137.6 (C), 141.6 (C), 142.1 (C), 142.5 (CH), 142.9 (C), 144.0 (C), 144.4 (CH), 144.9 (CH), 147.2 (CH), 149.9 (CH), 151.3 (CH), 169.1 (C);

HRMS (ESI+) m/z (%): calcd for C$_{47}$H$_{64}$ClN$_6$O$_4$ [M$^+$]: 755.4046, found: 755.4029.

3-(3-(10-(4-(8-acetoxy-5-chloroquinolin-7-yl)-1H-1,2,3-triazol-1-yl)decyloxy)propyl)-1-(6-(3-(pyridin-3-yl)propoxy)hexyl)pyridinium chloride (42)

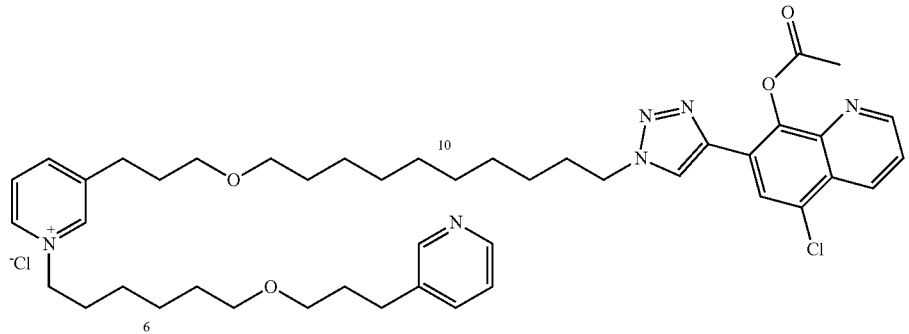

$C_{45}H_{60}Cl_2N_6O_4$
MM=818

Starting with the pyridine-pyridinium chloride 24 (119 mg, 0.21 mmol) and the TMS-protected acetylene 8 (82 mg, 0.19 mmol), the product 42 (70 mg, 41%) is obtained in the form of a brown oil. $R_f$=0.19 (10% MeOH/CH$_2$Cl$_2$); $^1$H NMR (400 MHz, CDCl$_3$) δ 1.24-1.44 (m, 16H), 1.46-1.57 (m, 4H), 1.86 (m, 2H), 1.93-2.08 (m, 6H), 2.58 (s, 3H), 2.69 (t, J=7.6 Hz, 2H), 2.98 (t, J=7.6 Hz, 2H), 3.33-3.40 (m, 6H), 3.42 (t, J=6.0 Hz, 2H), 4.47 (t, J=7.2 Hz, 2H), 4.97 (t, J=7.2 Hz, 2H), 7.24 (dd, J=7.6, 5.0 Hz, 1H), 7.51-7.57 (m, 2H), 8.00 (m, 1H), 8.04 (s, 1H), 8.22 (d, J=7.8 Hz, 1H), 8.42-8.46 (m, 2H), 8.52 (s, 1H), 8.54 (d, J=8.6 Hz, 1H), 8.94 (dd, J=5.0, 1.5 Hz, 1H), 9.36 (s, 1H), 9.45 (d, J=5.0 Hz, 1H); $^{13}$C NMR (100 MHz, CDCl$_3$) δ 21.4 (CH$_3$), 25.8 (CH$_2$), 26.0 (CH$_2$), 26.2 (CH$_2$), 26.5 (CH$_2$), 29.0 (CH$_2$), 29.4 (2×CH$_2$), 29.5 (2×CH$_2$), 29.6 (CH$_2$), 29.7 (2×CH$_2$), 30.2 (CH$_2$), 30.4 (CH$_2$), 30.9 (CH$_2$), 32.2 (CH$_2$), 50.7 (CH$_2$), 61.8 (CH$_2$), 69.0 (CH$_2$), 69.5 (CH$_2$), 70.6 (CH$_2$), 71.2 (CH$_2$), 122.5 (CH), 123.1 (CH), 123.6 (CH), 123.8 (C), 125.4 (CH$_2$), 126.7 (C), 127.9 (CH), 129.2 (C), 133.2 (CH), 136.4 (CH), 137.5 (C), 141.5 (C), 142.0 (C), 142.5 (CH), 143.0 (C), 143.9 (C), 144.4 (CH), 144.8 (CH), 147.1 (CH), 149.7 (CH), 151.3 (CH), 169.1 (C); LRMS (ESI+) m/z (%): 783 (1) [M$^+$]; 741 (100).

3-(3-(8-(4-(8-acetoxy-5-chloroquinolin-7-yl)-1H-1,2,3-triazol-1-yl)octyloxy)propyl)-1-(8-(3-(pyridin-3-yl)propoxy)octyl)pyridinium chloride (43)

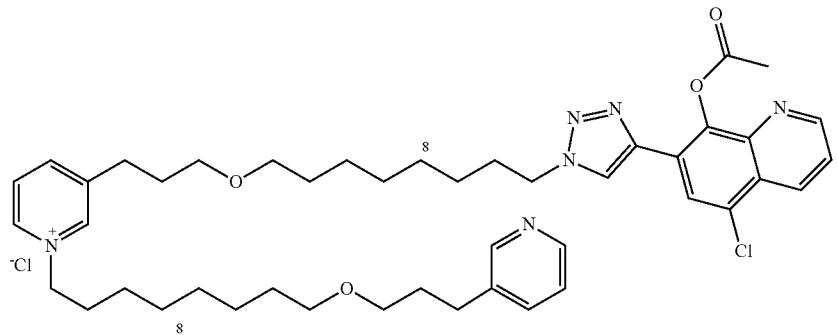

$C_{45}H_{60}Cl_2N_6O_4$
MM=818

Starting with the pyridine-pyridinium chloride 25 (87 mg, 0.15 mmol) and the TMS-protected acetylene 8 (62 mg, 0.19 mmol), the product 43 (45 mg, 36%) is obtained in the form of a brown oil. $R_f$=0.21 (10% MeOH/CH$_2$Cl$_2$); $^1$H NMR (400 MHz, CDCl$_3$) δ 1.22-1.41 (m, 18H), 1.47-1.57 (m, 4H), 1.87 (m, 2H), 1.93-2.07 (m, 6H), 2.58 (s, 3H), 2.70 (t, J=7.6 Hz, 2H), 2.97 (t, J=7.6 Hz, 2H), 3.33-3.45 (m, 8H), 4.48 (m, 2H), 4.96 (m, 2H), 7.29 (dd, J=7.6, 5.0 Hz, 1H), 7.50-7.57 (m, 2H), 7.99 (m, 1H), 8.04 (s, 1H), 8.22 (d, J=7.6 Hz, 1H), 8.41-8.46 (m, 2H), 8.52 (s, 1H), 8.54 (d, J=8.6 Hz, 1H), 8.94 (d, J=5.0 Hz, 1H), 9.36 (s, 1H), 9.43 (d, J=5.0 Hz, 1H); $^{13}$C NMR (100 MHz, CDCl$_3$) δ 21.4 (CH$_3$), 26.1 (CH$_2$), 26.2 (2×CH$_2$), 26.5 (CH$_2$), 29.0 (CH$_2$), 29.1 (CH$_2$), 29.2 (CH$_2$), 29.3 (CH$_2$), 29.6 (CH$_2$), 29.7 (CH$_2$), 29.8 (2×CH$_2$), 30.3 (CH$_2$), 30.4 (CH$_2$), 31.0 (CH$_2$), 32.2 (CH$_2$), 50.7 (CH$_2$), 61.9 (CH$_2$), 69.1 (CH$_2$), 69.5 (CH$_2$), 71.0 (CH$_2$), 71.1 (CH$_2$), 122.5 (CH), 123.1 (CH), 123.6 (CH), 123.9 (C), 125.4 (CH$_2$), 126.8 (C), 127.9 (CH), 129.2 (C), 133.2 (CH), 136.5 (CH), 137.6 (C), 141.6 (C), 142.1 (C), 142.6 (CH), 142.9 (C), 143.9 (C), 144.5 (CH), 144.8 (CH), 146.9 (CH), 149.6 (CH), 151.3 (CH), 169.2 (C); LRMS (ESI+) m/z (%): 783 (2) [M$^+$]; 741 (100).

3-(3-(12-(4-(8-acetoxy-5-chloroquinolin-7-yl)-1H-1,2,3-triazol-1-yl)dodecyloxy)propyl)-1-(4-(3-(pyridin-3-yl)propoxy)butyl)pyridinium chloride (44)

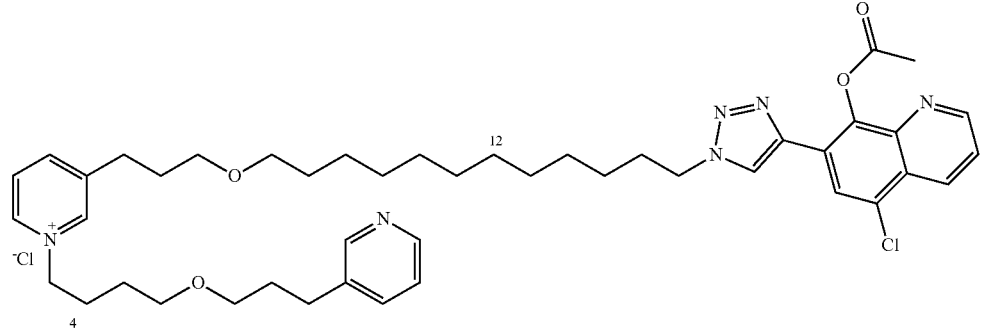

C$_{45}$H$_{60}$Cl$_2$N$_6$O$_4$
MM=818

Starting with the pyridine-pyridinium chloride 26 (89 mg, 0.16 mmol) and the TMS-protected acetylene 8 (62 mg, 0.20 mmol), the product 44 (53 mg, 42%) is obtained in the form of a brown oil. $R_f$=0.26 (10% MeOH/CH$_2$Cl$_2$); $^1$H NMR (400 MHz, CDCl$_3$) δ 1.17-1.41 (m, 16H), 1.51 (m, 2H), 1.64 (m, 2H), 1.86 (m, 2H), 1.92-2.02 (m, 6H), 2.13 (m, 2H), 2.58 (s, 3H), 2.67 (t, J=7.6 Hz, 2H), 2.98 (t, J=7.6 Hz, 2H), 3.33-3.47 (m, 8H), 4.46 (t, J=7.1 Hz, 2H), 5.01 (t, J=7.0 Hz, 2H), 7.24 (m, 1H), 7.50-7.57 (m, 2H), 7.96-8.04 (m, 2H), 8.22 (d, J=7.7 Hz, 1H), 8.22 (d, J=7.8 Hz, 1H), 8.37-8.49 (m, 2H), 8.52-8.57 (m, 2H), 8.94 (dd, J=4.2, 1.5 Hz, 1H), 9.37 (s, 1H), 9.47 (d, J=5.0 Hz, 1H); $^{13}$C NMR (100 MHz, CDCl$_3$) δ 21.4 (CH$_3$), 26.2 (CH$_2$), 26.3 (CH$_2$), 26.6 (CH$_2$), 29.1 (CH$_2$), 29.4 (2×CH$_2$), 29.5 (2×CH$_2$), 29.6 (2×CH$_2$), 29.8 (3×CH$_2$), 30.2 (CH$_2$), 30.4 (CH$_2$), 30.9 (CH$_2$), 50.7 (CH$_2$), 61.6 (CH$_2$), 69.0 (CH$_2$), 69.9 (CH$_2$), 70.0 (CH$_2$), 71.2 (CH$_2$), 122.5 (CH), 123.0 (CH), 123.7 (CH), 123.8 (C), 125.4 (CH$_2$), 126.7 (C), 127.9 (CH), 129.2 (C), 133.2 (CH), 136.3 (CH), 137.5 (C), 141.5 (C), 142.0 (C), 142.4 (C), 143.0 (C), 143.9 (C), 144.5 (CH), 144.9 (CH), 147.1 (CH), 149.7 (CH), 151.2 (CH), 169.0 (C); LRMS (ESI+) m/z (%): 873 (1) [M$^+$]; 741 (100).

3-(3-(6-(4-(8-acetoxy-5-chloroquinolin-7-yl)-1H-1,2,3-triazol-1-yl)hexyloxy)propyl)-1-(10-(3-(pyridin-3-yl)propoxy)decyl)pyridinium chloride (45)

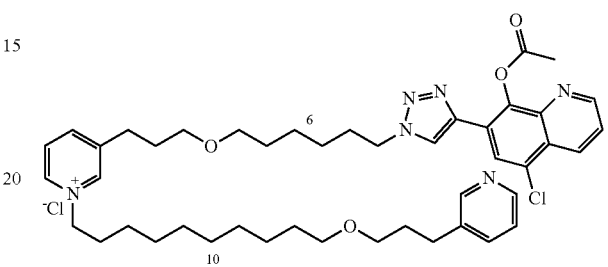

C$_{45}$H$_{60}$Cl$_2$N$_6$O$_4$
MM=818

Starting with the pyridine-pyridinium chloride 27 (145 mg, 0.25 mmol) and the TMS-protected acetylene 8 (104 mg, 0.33 mmol), the product 45 (97 mg, 47%) is obtained in the form of a brown oil. $R_f$=0.19 (10% MeOH/CH$_2$Cl$_2$); $^1$H NMR (400 MHz, acetone-d6) δ 1.15-1.41 (m, 16H), 1.42-1.55 (m, 4H), 1.83 (m, 2H), 1.92-2.09 (m, 6H), 2.65 (s, 3H), 2.69 (m, 2H), 2.97 (m, 2H), 3.30-3.44 (m, 8H), 4.66 (m, 2H), 4.97 (m, 2H), 7.29 (m, 1H), 7.61 (d, J=7.6 Hz, 1H), 7.71 (m, 1H), 8.11 (s, 1H), 8.40-8.66 (m, 5H), 8.97-9.04 (m, 2H), 9.45 (m, 1H), 9.68 (m, 1H); $^{13}$C NMR (100 MHz, CDCl$_3$) δ 21.5 (CH$_3$), 25.8 (CH$_2$), 26.3 (2×CH$_2$), 26.4 (CH$_2$), 29.2 (CH$_2$), 29.5 (2×CH$_2$), 29.6 (2×CH$_2$), 29.7 (2×CH$_2$), 29.9 (CH$_2$), 30.3 (CH$_2$), 30.4 (CH$_2$), 31.2 (CH$_2$), 32.2 (CH$_2$), 50.7 (CH$_2$), 62.1 (CH$_2$), 69.2 (CH$_2$), 69.6 (CH$_2$), 70.8 (CH$_2$), 71.2 (CH$_2$), 122.6 (CH), 123.2 (CH), 123.9 (CH, C), 125.5 (CH), 126.8 (C), 127.9 (CH), 129.3 (C), 133.3 (CH), 136.1 (CH), 137.7 (C), 141.6 (C), 142.1 (C), 142.6 (CH), 142.8 (C), 144.0 (C), 144.5 (CH), 144.9 (CH), 147.2 (CH), 149.9 (CH), 151.4 (CH), 169.2 (C); LRMS (ESI+) m/z (%): 783 (1) [M$^+$]; 741 (100).

3-(3-(6-(4-(8-acetoxy-5-chloroquinolin-7-yl)-1H-1,2,3-triazol-1-yl)hexyloxy)propyl)-1-(12-(3-(pyridin-3-yl)propoxy)dodecyl)pyridinium chloride (46)

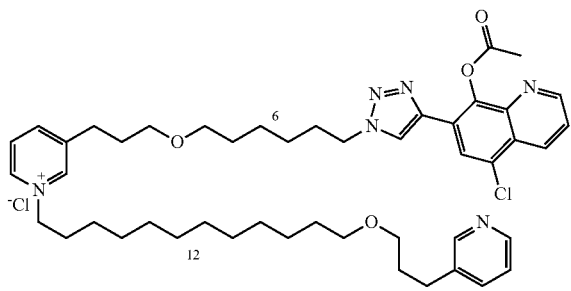

C$_{47}$H$_{64}$Cl$_2$N$_6$O$_4$
MM=846

Starting with the pyridine-pyridinium chloride 28 (89 mg, 0.15 mmol) and the TMS-protected acetylene 8 (59 mg, 0.18 mmol), the product 46 (42 mg, 34%) is obtained in the form of a brown oil. R$_f$=0.12 (10% MeOH/CH$_2$Cl$_2$); $^1$H NMR (400 MHz, CDCl$_3$) δ 1.20-1.40 (m, 20H), 1.46-1.64 (m, 4H), 1.88 (m, 2H), 1.95-2.10 (m, 6H), 2.61 (s, 3H), 2.71 (m, 2H), 2.98 (t, J=7.6 Hz, 2H), 3.32-3.48 (m, 8H), 4.55 (t, J=7.0 Hz, 2H), 4.94 (m, 2H), 7.27 (m, 1H), 7.52-7.60 (m, 2H), 7.94 (m, 1H), 8.16 (s, 1H), 8.22 (d, J=7.0 Hz, 1H), 8.40-8.58 (m, 4H), 8.95 (d, J=3.2 Hz, 1H), 9.23 (m, 1H), 9.27 (m, 1H); $^{13}$C NMR (100 MHz, CDCl$_3$) δ 21.6 (CH$_3$) 26.2 (2×CH$_2$) 26.7 (CH$_2$) 27.7 (CH$_2$) 29.2 (CH$_2$) 29.3 (2×CH$_2$) 29.7 (3×CH$_2$) 29.8 (3×CH$_2$) 29.9 (CH$_2$), 30.2 (CH$_2$), 31.0 (2×CH$_2$), 32.3 (CH$_2$), 50.6 (CH$_2$), 62.1 (CH$_2$), 69.4 (CH$_2$), 69.5 (CH$_2$), 70.1 (CH$_2$), 71.1 (CH$_2$) 122.6 (CH), 123.5 (CH), 123.9 (CH, C), 125.4 (CH), 126.9 (C), 127.9 (CH), 129.3 (C), 133.3 (CH), 136.9 (CH), 137.9 (C), 141.6 (C), 142.1 (C), 142.6 (CH, C), 144.0 (C), 144.8 (2×CH), 144.8 (CH), 146.7 (CH), 149.3 (CH), 151.4 (CH), 169.4 (C); HRMS (ESI+): calcd for C$_{47}$H$_{64}$ClN$_6$O$_4$ [M$^+$]: 811.4672, found: 811.4675.

3-(3-(8-(4-(8-acetoxy-5-chloroquinolin-7-yl)-1H-1,2,3-triazol-1-yl)octyloxy)propyl)-1-(10-(3-(pyridin-3-yl)propoxy)decyl)pyridinium chloride (47)

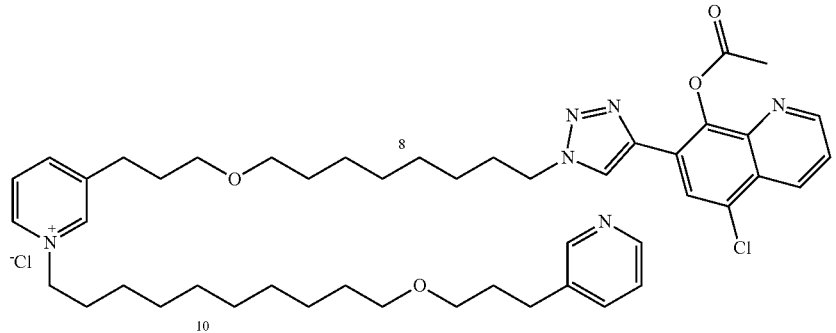

C$_{47}$H$_{64}$Cl$_2$N$_6$O$_4$
MM=846

Starting with the pyridine-pyridinium chloride 29 (27 mg, 0.045 mmol) and the TMS-protected acetylene 8 (14 mg, 0.018 mmol), the product 47 (29 mg, 77%) is obtained in the form of a brown oil. R$_f$=0.30 (10% MeOH/CH$_2$Cl$_2$); $^1$H NMR (400 MHz, CDCl$_3$) δ 1.17-1.42 (m, 22H), 1.47-1.63 (m, 4H), 1.89 (m, 2H), 1.94-2.07 (m, 6H), 2.59 (s, 3H), 2.72 (m, 2H), 2.99 (m, 2H), 3.33-3.48 (m, 8H), 4.49 (t, J=7.1 Hz, 2H), 4.94 (m, 2H), 7.27 (m, 1H), 7.51-7.59 (m, 2H), 8.01 (m, 1H), 8.06 (s, 1H), 8.25 (d, J=7.2 Hz, 1H), 8.50-8.58 (m, 2H), 8.95 (m, 1H), 9.24-9.37 (m, 2H); $^{13}$C NMR (100 MHz, CDCl$_3$) δ 21.5 (CH$_3$), 26.1 (CH$_2$), 26.2 (CH$_2$), 26.3 (CH$_2$), 26.5 (CH$_2$), 28.9 (CH$_2$), 29.2 (CH$_2$), 29.0 (CH$_2$), 29.2 (CH$_2$), 29.5 (CH$_2$), 29.6 (3×CH$_2$), 29.7 (CH$_2$), 29.8 (CH$_2$), 29.9 (CH$_2$), 30.3 (CH$_2$), 30.4 (CH$_2$), 31.1 (CH$_2$), 32.2 (CH$_2$), 50.7 (CH$_2$), 62.0 (CH$_2$), 69.1 (CH$_2$), 69.5 (CH$_2$), 71.1 (CH$_2$), 71.2 (CH$_2$), 122.5 (CH), 123.2 (CH), 123.9 (CH, C), 125.4 (CH$_2$), 126.8 (C), 128.0 (CH), 129.2 (C), 133.2 (CH), 136.3 (CH), 137.6 (C), 141.6 (C), 142.1 (C), 142.5 (CH), 142.7 (C), 143.9 (C), 144.3 (CH), 145.1 (CH), 147.2 (CH), 149.8 (CH), 151.3 (CH), 169.1 (C); LRMS (ESI+) m/z (%): 811 (1) [M$^+$]; 769 (100).

3-(3-(10-(4-(8-acetoxy-5-chloroquinolin-7-yl)-1H-1, 2,3-triazol-1-yl)decyloxy)propyl)-1-(10-(3-(pyridin-3-yl)propoxy)decyl)pyridinium chloride (48)

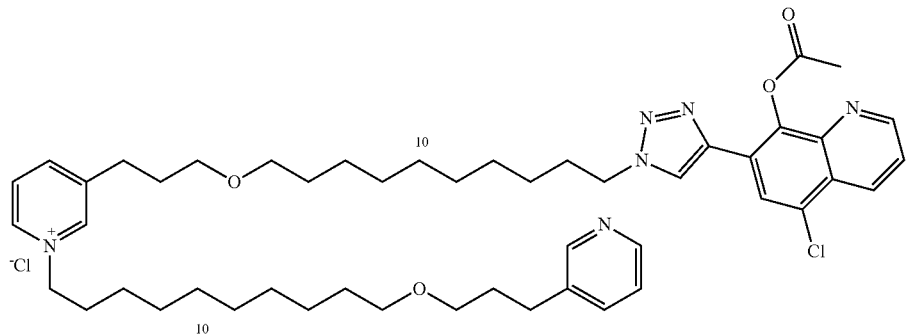

$C_{49}H_{68}Cl_2N_6O_4$
MM=874

Starting with the pyridine-pyridinium chloride 30 (130 mg, 0.21 mmol) and the TMS-protected acetylene 8 (85 mg, 0.27 mmol), the product 48 (110 mg, 61%) is obtained in the form of a brown oil. $R_f$=0.33 (10% MeOH/CH$_2$Cl$_2$); $^1$H NMR (400 MHz, CDCl$_3$) δ 1.18-1.40 (m, 24H), 1.46-1.60 (m, 4H), 1.88 (m, 2H), 1.93-2.06 (m, 6H), 2.58 (s, 3H), 2.70 (t, J=7.6 Hz, 2H), 2.98 (t, J=7.6 Hz, 2H), 3.32-3.44 (m, 8H), 4.47 (t, J=7.2 Hz, 2H), 4.94 (m, 2H), 7.23 (dd, J=7.6, 5.0 Hz, 1H), 7.51-7.54 (m, 2H), 7.98-8.09 (m, 2H), 8.23 (d, J=7.7 Hz, 1H), 8.40-8.50 (m, 2H), 8.51-8.56 (m, 2H), 8.94 (dd, J=5.0, 1.5 Hz, 1H), 9.34 (s, 1H), 9.42 (m, 1H); $^{13}$C NMR (100 MHz, CDCl$_3$) δ 21.3 (CH$_3$), 26.1 (2×CH$_2$), 26.2 (CH$_2$), 26.5 (CH$_2$), 28.9 (CH$_2$), 29.1 (CH$_2$), 29.3 (CH$_2$), 29.4 (2×CH$_2$), 29.5 (3×CH$_2$), 29.6 (CH$_2$), 29.7 (2×CH$_2$), 29.8 (CH$_2$), 30.2 (CH$_2$), 30.4 (CH$_2$), 31.0 (CH$_2$), 32.1 (CH$_2$), 50.6 (CH$_2$), 61.8 (CH$_2$), 68.9 (CH$_2$), 69.4 (CH$_2$), 71.0 (CH$_2$), 71.1 (CH$_2$), 122.4 (CH), 123.0 (CH), 123.5 (CH), 123.8 (C), 125.3 (CH$_2$), 126.6 (C), 127.9 (CH), 129.1 (C), 133.1 (CH), 136.3 (CH), 137.5 (C), 141.4 (C), 142.0 (C), 142.4 (CH), 142.9 (C), 143.8 (C), 144.3 (CH), 144.8 (CH), 147.0 (CH), 149.6 (CH), 151.2 (CH), 169.0 (C); LRMS (ESI+) m/z (%): 839 (1) [M$^+$]; 811 (100).

3-(3-(12-(4-(8-acetoxy-5-chloroquinolin-7-yl)-1H-1, 2,3-triazol-1-yl)dodecyloxy)propyl)-1-(8-(3-(pyridin-3-yl)propoxy)octyl)pyridinium chloride (49)

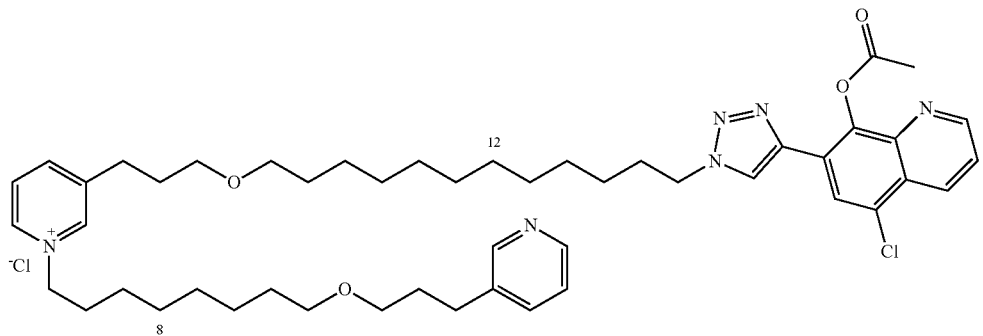

$C_{49}H_{68}Cl_2N_6O_4$
MM=874

Starting with the pyridine-pyridinium chloride 31 (109 mg, 0.17 mmol) and the TMS-protected acetylene 8 (68 mg, 0.19 mmol), the product 49 (95 mg, 63%) is obtained in the form of a brown oil. $R_f$=0.25 (10% MeOH/CH$_2$Cl$_2$); $^1$H NMR (400 MHz, CDCl$_3$) δ 1.20-1.40 (m, 24H), 1.46-1.57 (m, 4H), 1.88 (m, 2H), 1.92-2.07 (m, 6H), 2.58 (s, 3H), 2.70 (t, J=7.6 Hz, 2H), 2.98 (t, J=7.6 Hz, 2H), 3.32-3.46 (m, 8H), 4.46 (t, J=7.1 Hz, 2H), 4.95 (m, 2H), 7.24 (m, 1H), 7.50-7.57 (m, 2H), 7.96-8.04 (m, 2H), 8.23 (d, J=7.7 Hz, 1H), 8.42-8.53 (m, 2H), 8.53-8.58 (m, 2H), 8.94 (m, 1H), 9.30 (s, 1H), 9.42 (m, 1H); $^{13}$C NMR (100 MHz, CDCl$_3$) δ 21.4 (CH$_3$), 26.1 (2×CH$_2$), 26.2 (CH$_2$), 26.6 (CH$_2$), 29.0 (CH$_2$), 29.2 (CH$_2$), 29.4 (CH$_2$), 29.5 (2×CH$_2$), 29.6 (3×CH$_2$), 29.7 (3×CH$_2$), 30.2 (CH$_2$), 30.4 (CH$_2$), 31.0 (CH$_2$), 32.1 (CH$_2$), 50.7 (CH$_2$), 61.9 (CH$_2$), 69.0 (CH$_2$), 69.5 (CH$_2$), 70.1 (CH$_2$), 71.2 (CH$_2$), 122.5 (CH), 123.0 (CH), 123.8 (CH, C), 125.4 (CH$_2$), 126.7 (C), 127.9 (CH), 129.1 (C), 133.2 (CH), 136.2 (CH), 137.5 (C), 141.5 (C), 142.0 (C), 142.4 (CH), 143.0 (C), 143.8 (C), 144.3 (CH), 144.9 (CH), 147.1 (CH), 149.8 (CH), 151.2 (CH), 169.0 (C); LRMS (ESI+) m/z (%): 839 (1) [M]$^+$; 797 (100); HRMS (ESI+) m/z (%): calcd for C$_{49}$H$_{68}$ClN$_6$O$_4$ [M$^+$]: 839.4985, found: 839.4879.

3-(3-(10-(4-(8-acetoxy-5-chloroquinolin-7-yl)-1H-1,2,3-triazol-1-yl)decyloxy)propyl)-1-(12-(3-(pyridin-3-yl)propoxy)dodecyl)pyridinium chloride (50)

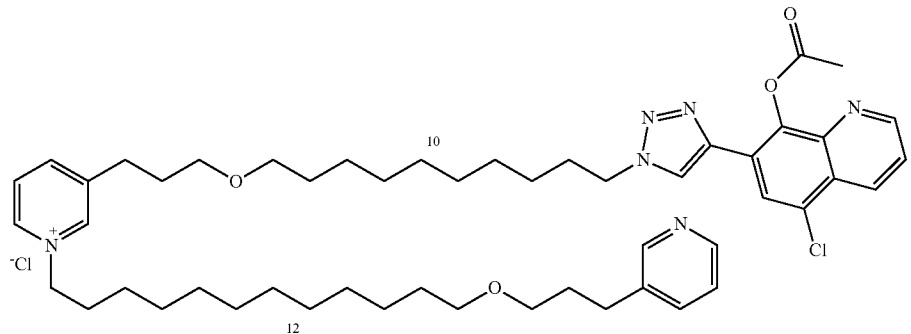

C$_{51}$H$_{72}$Cl$_2$N$_6$O$_4$
MM=902

Starting with the pyridine-pyridinium chloride 32 (86 mg, 0.17 mmol) and the TMS-protected acetylene 8 (66 mg, 0.21 mmol), the product 50 (54 mg, 42%) is obtained in the form of a brown oil. $R_f$=0.28 (10% MeOH/CH$_2$Cl$_2$); $^1$H NMR (400 MHz, CDCl$_3$) δ 1.17-1.42 (m, 28H), 1.46-1.52 (m, 4H), 1.88 (m, 2H), 1.92-2.07 (m, 6H), 2.58 (s, 3H), 2.70 (m, 2H), 2.98 (t, J=7.6 Hz, 2H), 3.33-3.46 (m, 8H), 4.47 (t, J=7.1 Hz, 2H), 4.93 (t, J=7.0 Hz, 2H), 7.23 (m, 1H), 7.54 (m, 2H), 7.97-8.06 (m, 2H), 8.22 (d, J=7.7 Hz, 1H), 8.40-8.48 (m, 2H), 8.51-8.58 (m, 2H), 8.94 (dd, J=5.0, 1.5 Hz, 1H), 9.28 (s, 1H), 9.39 (m, 1H); $^{13}$C NMR (100 MHz, CDCl$_3$) δ 21.4 (CH$_3$), 26.2 (2×CH$_2$), 26.3 (CH$_2$), 26.5 (CH$_2$), 29.0 (CH$_2$), 29.2 (CH$_2$), 29.4 (4×CH$_2$), 29.5 (2×CH$_2$), 29.6 (CH$_2$), 29.7 (2×CH$_2$), 29.8 (3×CH$_2$), 30.2 (CH$_2$), 30.4 (CH$_2$), 31.1 (CH$_2$), 32.2 (CH$_2$), 50.7 (CH$_2$), 62.0 (CH$_2$), 69.0 (CH$_2$), 69.5 (CH$_2$), 71.1 (CH$_2$), 71.2 (CH$_2$), 122.5 (CH), 123.1 (CH), 123.5 (CH), 123.9 (C), 125.4 (CH$_2$), 126.7 (C), 128.0 (CH), 129.2 (C), 133.2 (CH), 136.2 (CH), 137.5 (C), 141.5 (C), 142.0 (C), 142.5 (CH), 142.9 (C), 143.8 (C), 144.3 (CH), 144.9 (CH), 147.2 (CH), 149.9 (CH), 151.3 (CH), 169.1 (C); LRMS (ESI+) m/z (%): 867 (1) [M$^+$]; 825 (100).

3-(3-(12-(4-(8-acetoxy-5-chloroquinolin-7-yl)-1H-1,2,3-triazol-1-yl)dodecyloxy)propyl)-1-(10-(3-(pyridin-3-yl)propoxy)decyl)pyridinium chloride (51)

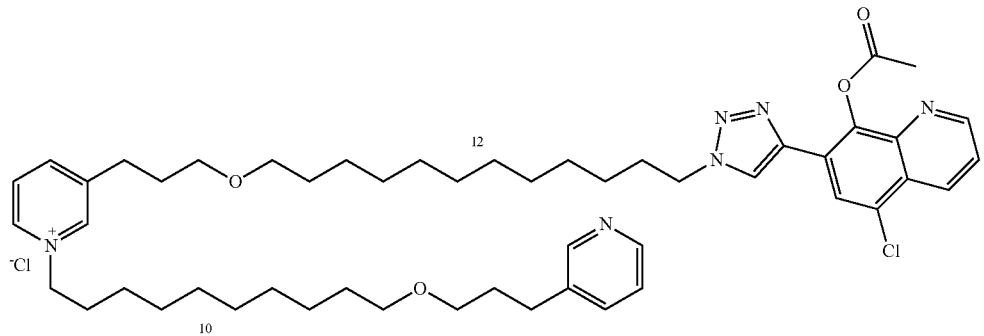

$C_{51}H_{72}Cl_2N_6O_4$
MM=904

Starting with the pyridine-pyridinium chloride 33 (71 mg, 0.11 mmol) and the TMS-protected acetylene 8 (44 mg, 0.14 mmol), the product 51 (50 mg, 51%) is obtained in the form of a brown oil. $R_f$=0.22 (10% MeOH/CH$_2$Cl$_2$); $^1$H NMR (400 MHz, CDCl$_3$) δ 1.19-1.40 (m, 28H), 1.48-1.61 (m, 4H), 1.89 (m, 2H), 1.94-2.05 (m, 6H), 2.58 (s, 3H), 2.70 (m, 2H), 2.99 (t, J=7.6 Hz, 2H), 3.34-3.47 (m, 8H), 4.46 (t, J=7.1 Hz, 2H), 4.95 (m, 2H), 7.23 (m, 1H), 7.50-7.58 (m, 2H), 7.96-8.03 (m, 2H), 7.96-8.03 (m, 2H), 8.22 (d, J=7.7 Hz, 1H), 8.42-8.52 (m, 2H), 8.53-8.59 (m, 2H), 8.95 (m, 1H), 9.23 (s, 1H), 9.38 (m, 1H); $^{13}$C NMR (100 MHz, CDCl$_3$) δ 21.4 (CH$_3$), 26.3 (3×CH$_2$), 26.6 (CH$_2$), 29.1 (CH$_2$), 29.2 (CH$_2$), 29.5 (2×CH$_2$), 29.7 (6×CH$_2$), 29.8 (3×CH$_2$), 29.9 (CH$_2$), 30.3 (CH$_2$), 30.5 (CH$_2$), 31.1 (CH$_2$), 32.2 (CH$_2$), 50.8 (CH$_2$), 62.1 (CH$_2$), 69.0 (CH$_2$), 69.6 (CH$_2$), 71.2 (CH$_2$), 71.3 (CH$_2$), 122.5 (CH), 123.0 (CH), 123.7 (CH), 123.9 (C), 125.5 (CH$_2$), 126.8 (C), 128.0 (CH), 129.3 (C), 133.3 (CH), 136.2 (CH), 137.6 (C), 141.6 (C), 142.1 (C), 142.5 (CH), 143.0 (C), 143.9 (C), 144.3 (C), 144.9 (CH), 147.2 (CH), 149.9 (CH), 151.3 (CH), 169.1 (C);

LRMS (ESI+) m/z (%): 867 (1) [M$^+$]; 825 (100).

3-(3-(12-(4-(8-acetoxy-5-chloroquinolin-7-yl)-1H-1,2,3-triazol-1-yl)dodecyloxy)propyl)-1-(12-(3-(pyridin-3-yl)propoxy)dodecyl)pyridinium chloride (52)

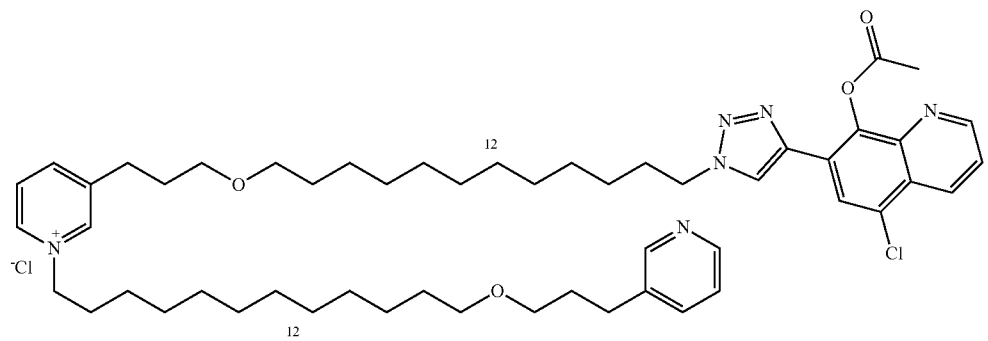

$C_{53}H_{76}Cl_2N_6O_4$
MM=930

Starting with the pyridine-pyridinium chloride 34 (84 mg, 0.12 mmol) and the TMS-protected acetylene 8 (50.5 mg, 0.16 mmol), the product 52 (79 mg, 70%) is obtained in the form of a brown oil. $R_f$=0.26 (10% MeOH/CH$_2$Cl$_2$); $^1$H NMR (400 MHz, CDCl$_3$) δ 1.18-1.41 (m, 32H), 1.47-1.59 (m, 4H), 1.88 (m, 2H), 1.92-2.07 (m, 6H), 2.58 (s, 3H), 2.77 (m, 2H), 2.98 (m, 2H), 3.33-3.45 (m, 8H), 4.47 (t, J=7.1 Hz, 2H), 4.93 (m, 2H), 7.50-7.68 (m, 3H), 7.97-8.09 (m, 2H), 8.23 (d, J=6.7 Hz, 1H), 8.39-8.51 (m, 2H), 8.51-8.58 (m, 2H), 8.94 (m, 1H), 9.28 (s, 1H), 9.39 (m, 1H); $^{13}$C NMR (100 MHz, CDCl$_3$) δ 21.3 (CH$_3$), 26.2 (3×CH$_2$), 26.5 (CH$_2$), 29.0 (CH$_2$), 29.1 (CH$_2$), 29.3 (CH$_2$), 29.4 (2×CH$_2$), 29.5 (5×CH$_2$), 29.6 (CH$_2$), 29.7 (CH$_2$), 29.8 (2×CH$_2$), 30.2 (CH$_2$), 30.4 (CH$_2$), 31.1 (CH$_2$), 32.1 (CH$_2$), 50.7 (CH$_2$), 62.0 (CH$_2$), 69.0 (CH$_2$), 69.5 (CH$_2$) 71.1 (CH$_2$), 71.2 (CH$_2$), 122.4 (CH), 123.0 (CH), 123.8 (CH, C) 125.4 (CH$_2$), 126.7 (C), 127.9 (CH), 129.1 (C), 133.3 (CH), 135.3 (CH), 135.5 (C), 141.5 (C), 142.0 (C), 142.4 (CH), 142.9 (C), 143.8 (C), 144.3 (CH), 144.9 (CH), 147.2 (CH), 149.8 (CH), 151.2 (CH), 169.0 (C); LRMS (ESI+) m/z (%): 895 (1) [M$^+$]; 853 (100).

The invention claimed is:

1. A compound of formula (A):

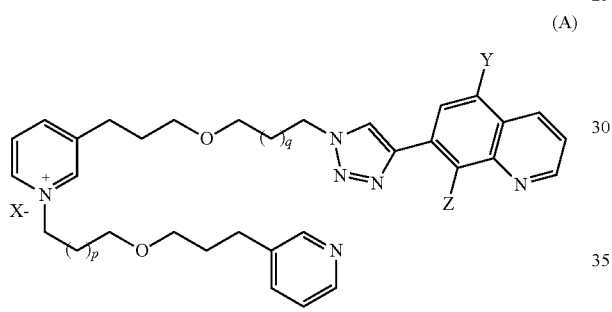

(A)

characterized in that:
X is a halogen;
Y is a halogen;
Z is a hydroxy or amine group or an —OR$_1$ group wherein R$_1$ is a C$_1$-C$_4$ alkyl or a C$_1$-C$_4$ acyl;
p is an integer and 13>p≥2; and
q is an integer and 13>q≥2;
on the condition that:
if p=4, then q≠8;
if p=10, then q≠4; and
if p=8, then q≠6.

2. The compound of formula (A) according to claim 1 characterized in that:
p=2 and q=2, 4 or 10;
p=4 and q=2, 4 or 6;
p=6 and q=2, 4, 6 or 10; or
p=8 and q=4 or 8.

3. The compound of formula (A) according to claim 1 characterized in that:
Z is —OH or OAc;
Y is Cl;
X is Cl; and
p and q are even numbers.

4. The compound of formula (A) according to claim 3 characterized in that:
p=2 and q=2, 4 or 10;
p=4 and q=2, 4 or 6;
p=6 and q=2, 4, 6 or 10; or
p=8 and q=4 or 8.

5. A process for producing the compound of formula (A) characterized in that the compound of formula B:

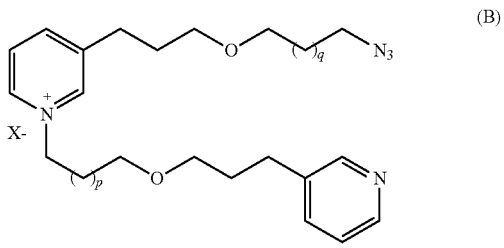

(B)

wherein
X is a halogen or Cl;
p is an integer and 13>p≥2;
q is an integer and 13>q≥2;
on the condition that:
if p=4, then q≠8;
if p=10, then q≠4; and
if p=8, then q≠6; or
p and q are even numbers;
is reacted in the presence of a catalyst, with the compound of formula C:

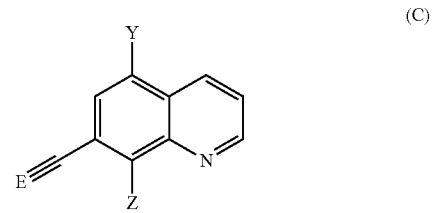

(C)

wherein
Y is a halogen or Cl;
Z is a hydroxy or amine group or an —OR$_1$ group wherein R$_1$ is a C$_1$-C$_4$ alkyl or a C$_1$-C$_4$ acyl or —OH or OAc;
and E is a leaving group selected from the group consisting of trimethylsilyl, tri-isopropyl silyl (TIPS) and dimethyl alcohol.

6. A medicinal product comprising a compound of formula (A) according to claim 1.

7. A medicinal product comprising a compound of formula (A) according to claim 3.

8. A method for preventing and/or treating a pathogenic infection caused by *Pseudomonas aeruginosa* comprising administering to a patient in need thereof a compound of formula (A) according to claim 1.

9. A method for preventing and/or treating a pathogenic infection caused by *Pseudomonas aeruginosa* comprising administering to a patient in need thereof a compound of formula (A) according to claim 1, wherein the pathogenic infection is a nosocomial infection.

10. A method for preventing and/or treating a pathogenic infection caused by *Pseudomonas aeruginosa* comprising administering to a patient in need thereof a compound of formula (A) according to claim 3.

11. A method for preventing and/or treating a pathogenic infection caused by *Pseudomonas aeruginosa* comprising administering to a patient in need thereof a compound of formula (A) according to claim 3, wherein the pathogenic infection is a nosocomial infection.

* * * * *